United States Patent [19]

Hubele et al.

[11] Patent Number: 5,376,657
[45] Date of Patent: Dec. 27, 1994

[54] MICROBICIDES

[75] Inventors: Adolf Hubele, Magden; Bernard Hostettler, Zurich; Marius Sutter, Binningen; Urs Müller, Münchenstein, all of Switzerland

[73] Assignee: Ciba-Geigy Corporation, Ardsley, N.Y.

[21] Appl. No.: 65,312

[22] Filed: May 21, 1993

Related U.S. Application Data

[62] Division of Ser. No. 988,496, Dec. 10, 1992, abandoned.

[51] Int. Cl.⁵ .................. A01N 43/58; A01N 43/54; C07D 401/12; C07D 403/12
[52] U.S. Cl. ..................... 514/253; 514/269; 514/272; 514/274; 514/338; 514/369; 514/372; 514/395; 544/238; 544/300; 544/310; 544/316; 544/317; 544/319; 544/321; 544/405; 546/271; 548/181; 548/183; 548/186; 548/213; 548/304.7; 548/306.1
[58] Field of Search .............. 514/253, 269, 272, 274, 514/338, 369, 372, 395; 544/238, 300, 310, 316, 405, 317, 319, 321; 546/271; 548/181, 213, 306.1, 304.7

[56] References Cited

U.S. PATENT DOCUMENTS

| | | | |
|---|---|---|---|
| 4,196,125 | 4/1980 | Paget et al. | 548/181 |
| 4,401,817 | 8/1983 | Paget et al. | 548/181 |
| 4,536,502 | 8/1985 | Giraudon et al. | 548/306.1 |
| 4,622,323 | 11/1986 | Giraudon et al. | 514/395 |

FOREIGN PATENT DOCUMENTS 0181826  5/1986  European Pat. Off. .
2607811  10/1988  France .

*Primary Examiner*—Emily Bernhardt
*Attorney, Agent, or Firm*—Edward McC. Roberts

[57] ABSTRACT

Benzimidazolesulfonic acid derivatives of the formula I

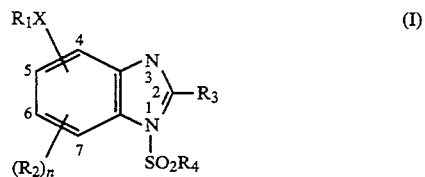

in which $R_1$ is an unsaturated 5-membered heterocycle having not more than two hetero atoms N and/or S or is an unsaturated 6-membered heterocycle having not more than two N atoms, it being possible for each of the heterocycles to be substituted, and X is oxygen or sulfur, while $R_2$, $R_3$, $R_4$ and n are as defined herein, are valuable microbicides. They can be used in crop protection in the form of suitable compositions, for example for controlling fungal disease.

24 Claims, No Drawings

MICROBICIDES

This application is a division of Ser. No. 07/988,496, field Dec. 10, 1992, now abandoned.

The present invention relates to novel benzimidazole-sulfonic acid derivatives of the formula I below. Furthermore, it relates to the preparation of these substances and to agrochemical compositions which comprise, as active ingredient, at least one of these compounds. Equally, the invention relates to the preparation of the compositions mentioned and to the use of the active ingredients or of the compositions for controlling or preventing attack of plants by phytopathogenic microorganisms, preferably fungi.

The compounds according to the invention are those of the general formula I

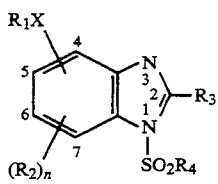

in which the $R_4SO_2$ group occupies the 1- or 3-position and, relative to the substituents $R_1X-$ and $R_2$, forms pure or mixed positional isomers, and in which the substituents are defined as follows:

$R_1$ is an unsaturated 5-membered heterocycle having not more than two hetero atoms N and/or S, or an unsaturated 6-membered heterocycle having not more than two N atoms, it being possible for each of the heterocycles to be unsubstituted or substituted by at least one of the substituents halogen, $C_1$–$C_3$alkyl, $C_1$–$C_3$alkoxy, $C_1$–$C_3$haloalkyl, $C_1$–$C_3$haloalkoxy, $COOC_1$–$C_3$alkyl, $C_3$–$C_6$cycloalkyl, CN and nitro;

$R_2$ radicals, identical or different, are halogen, $C_1$–$C_3$alkyl, $C_1$–$C_3$alkoxy, $C_1$–$C_3$haloalkyl, $C_1$–$C_3$haloalkoxy, nitro;

$R_3$ is cyano, $-CS-NH_2$ or $-C(SR')=NH$, where R' is $C_1$–$C_4$alkyl, $C_1$–$C_4$haloalkyl, or benzyl which is unsubstituted or substituted by halogen and/or $CF_3$;

$R_4$ is $C_1$–$C_4$alkyl, $C_3$–$C_6$cycloalkyl, $-N(R'')(R''')$, in which R'' and R''' are identical or different $C_1$–$C_3$alkyl radicals;

X is oxygen or sulfur; and n is an integer 0, 1 or 2.

The term alkyl itself or as part of another substituent such as haloalkyl, alkoxy or haloalkoxy, is understood as meaning for example the following straight-chain or branched groups, depending on the number of the carbon atoms indicated: methyl, ethyl, propyl, butyl as well as their isomers, isopropyl, isobutyl, sec-butyl, tert-butyl. Halogen and halo are fluorine, chlorine, bromine or iodine. Haloalkoxy therefore is a mono- to perhalogenated alkoxy radical, for example, inter alia, $OCH_2F$, $OCHF_2$, $OCHFCH_3$, $OCH_2CH_2Br$ or $OCF_2CHFCl$.

The term cycloalkyl represents cyclopropyl, cyclobutyl, cyclopentyl or cyclohexyl.

The unsaturated 5-membered heterocycles indicated are understood as meaning pyrrole, thiophene, pyrazole, imidazole, thiazole and isothiazole, and the corresponding 6-membered heterocycle is understood as meaning pyridine, pyrimidine, pyrazine and pyridazine.

The compounds of the formula I are oils or solids which are stable at room temperature and which are distinguished by valuable microbicidal properties. They can be used preventively and curatively in the agrocultural sector or in related fields for the control of plant-injurious microorganisms. Applied at low concentrations, the active ingredients of the formula I according to the invention are distinguished not only by an outstanding microbicidal, in particular fungicidal, action, but also by the fact that they are particularly well tolerated by plants.

Important compounds within the scope of the formula I are those in which $R_1$ is an unsubstituted or substituted pyridine, pyrimidine, pyrazine or pyridazine ring [sub-group Ib], and, from amongst these, those compounds in which the 6-membered heterocycle is substituted by one to three substituents selected from amongst halogen, methyl, ethyl, isopropyl, methoxy, $C_1$–$C_2$haloalkyl where halogen is F and/or Cl, $CF_3O$, $CHF_2O$ or nitro [sub-group Ic].

One of the particularly important substance groups within the scope of sub-group Ic is that in which the 6-membered heterocycle is unsubstituted or mono- to trisubstituted pyridine and $R_2$ radicals, identical or different, are fluorine, chlorine, bromine, methyl, methoxy, $CF_3$, $CF_3O$ or $CHF_2O$ where n=0, 1 or 2 [sub-group Id], in particular those where n=0 or 1 [sub-group Ie]. Particularly important substance groups within the scope of sub-group Id are those where $R_2$ equal halogen or $C_1$–$C_2$haloalkyl [sub-group Id'], especially those in which the pyridine ring is substituted by $CF_3$ [sub-group Id''].

Another important substance group within the scope of sub-group Ic is that in which the 6-membered heterocycle is unsubstituted or halo-substituted or haloalkyl-substituted pyrimidine and $R_2$ is fluorine, chlorine, bromine, methyl, methoxy or $CF_3$, n being 0, 1 or 2 [sub-group If]. Particularly important within the scope of sub-group If are those compounds in which $R_2$ is fluorine, chlorine, bromine, methyl, methoxy or $CF_3$, where n is 0, 1 or 2 [sub-group If'], and the substance group in which the pyrimidine is linked in the 4-position [sub-group If''].

Preferred compounds within the scope of sub-group Id in which $R_1$ is a 6-membered heterocycle are those in which $R_4$ is methyl, dimethylamino, cyclopropyl, cyclopentyl or cyclohexyl [sub-group Ig], in particular those in which $R_4$ is methyl [sub-group Ig'] or those in which $R_4$ is dimethylamino [sub-group Ig''].

Other important compounds within the scope of the formula I are those in which X is oxygen, those in which X is sulfur and $R_1$ is an unsubstituted or substituted pyrrole, thiophene, thiazole, isothiazole, imidazole or pyrazole ring [sub-group Ii].

From amongst these compounds, those in which the 5-membered heterocycle is substituted by halogen and/or methyl [sub-group Ij] are preferred, in particular those in which $R_2$, identical or different, are halogen, methyl, methoxy, $CF_3$, $CF_3O$ or $CHF_2O$, n being 0, 1 or 2 [sub-group Ik]. Important compounds are, for example, those without substituents $R_2$ (i.e. n=0).

Important compounds within the scope of the formula I are those in which $R_3$ is cyano or $C(S)NH_2$ [sub-group Im] or those in which $XR_1$ occupies the 5/6-position in the benzimidazole ring [sub-group In].

Important compounds of the formula I are those in which X is oxygen, including sub-groups Ib to In. Preferred individual compounds within the scope of sub-group Id are, for example, a) 1(3)-(dimethylaminosulfonyl)-2-cyano-4-bromo-6-(3,5-dichloropyridin-2-yloxy)-benzimidazole [Comp. 1.23];
b) 1(3)-methanesulfonyl-2-cyano-6-(5-trifluoromethyl-pyridin-2-yloxy)-benzimidazole [Comp. 1.21];
c) 1(3)-methanesulfonyl-2-cyano-6-(3-chloro-5-trifluoromethylpyridin-2-yloxy)-benzimidazole [Comp. 1.66];
d) 1(3)-cyclopropanesulfonyl-2-cyano-6-(3-chloro-5-trifluoromethylpyridin-2-yloxy)-benzimidazole [Comp. 1.74].

The compounds of the formula I can be prepared by reacting a compound of the formula II

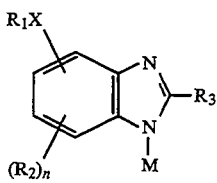

with a compound of the formula III

Q—SO$_2$—R$_4$             (III)

in which R$_1$, R$_2$, R$_3$, R$_4$, X and n are as defined under formula I and M is hydrogen or an alkali metal, preferably Na, K or Li, and Q is a halogen atom, preferably chlorine or bromine, or the radical O—SO$_2$—R$_4$, in an inert solvent, if appropriate in the presence of a base, at temperatures from −30° to +180° C., preferably −10° to 80° C., under atmospheric pressure, reduced or increased pressure, preferably atmospheric pressure.

Suitable solvents are mainly polar reaction media, such as ketones on their own (for example acetone, methyl ethyl ketone, tert-butyl methyl ketone) or as mixtures with ethers (such as diethyl ether, dioxane, tetrahydrofuran, 1,2-dimethoxyethane) or, for example, with dimethylformamide or dimethyl sulfoxide. It is expedient to react the benzimidazole derivative II in the presence of a strong inorganic base (such as KOH, NaOH).

Due to the reactivity of the thioamide group [R$_3$=—CSNH$_2$] or of the substituted isothioamide group [R$_3$=—C(—SR′)=NH], it is expedient to carry out the procedure in such a way that these groups are introduced in the last reaction step after the sulfonylation. Thus, in this case, the sulfonylated 2-cyanobenzimidazole of the formula I′

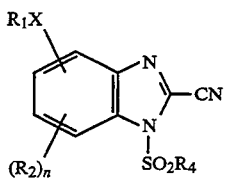

is reacted afterwards either with H$_2$S or HS-R′, R′ being defined as indicated for formula I. The reaction which leads to the thioamide [R$_3$=—CSNH$_2$] is carried out in polar solvents (for example alcohols, such as ethanol), but preferably in dimethylformamide (DMF) or in ethers (for example diethyl ether, tetrahydrofuran) or acetonitrile or in pyridine, using a ten-amine such as trialkylamine. H$_2$S is passed in at −20° to +80° C., in particular −10° to +40° C.

To prepare the substituted isothioamide group, a procedure can expediently be followed in such a way that the sulfonylated 2-cyanobenzimidazole of the formula I′ is treated with the thiol HS-R′ in a polar aprotic solvent (such as acetonitrile) in the presence of weak bases (such as alkali metal carbonate) at −20° to +100° C., preferably −10° to +40° C.

The 2-cyanobenzimidazole derivatives of the formula II are prepared by methods known per se from o-phenylenediamine derivatives or salts thereof:

a) 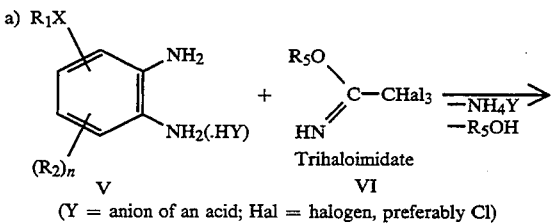

(Y = anion of an acid; Hal = halogen, preferably Cl)

b) 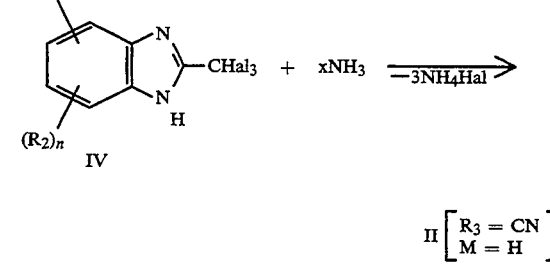

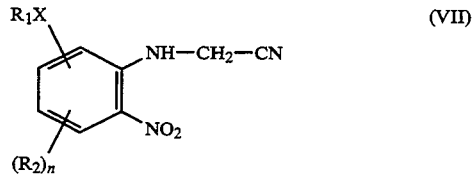

HY is an acid, preferably a hydrohalic acid, or sulfuric acid. However, the o-phenylenediamine derivative can also be used in the form of the free base when reaction step a) is carried out in glacial acetic acid. Preferred solvents are glacial acetic acid; ethers such as diethyl ether, dioxane, 1,2-dimethoxyethane; esters such as ethyl acetate or alcohols such as methanol and ethanol.

The trihaloimidate (for example methyl trichloro- or chlorodifluoro-methylimidate) is expediently added to the dissolved or suspended o-phenylenediamine derivative at −20° C. to +100° C. In reaction step b), the 2-trihalomethylbenzimidazole derivative obtained is expediently added to a concentrated aqueous ammonia solution (U.S. Pat. No. 3 576 818).

The 2-cyanobenzimidazole derivatives of the formula II can also be prepared with the corresponding o-nitroaniline derivative instead of the o-phenylenediamine derivative by reaction with formaldehyde and KCN in glacial acetic acid with an addition of zinc chloride (or another Lewis acid) as catalyst, giving compounds of the formula VII

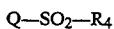

[K. Dimroth et al., Ber. 98, 3902 (1965)], which can be cyclised with K$_2$CO$_3$ to give 1-hydroxy-2-cyanobenzimidazole derivatives [B. Serafinowa et al. Rocz. Chem. 51, 1783 (1977)] and reacted with $PCl_3$ to give compounds of the formula II (M=hydrogen: $R_3$=CN).

The intermediates of the formula II in which $R_3$=CN and M=hydrogen are novel and are a further object of the present invention. (Compound group II').

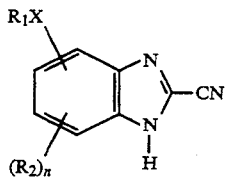

Compounds of the formula V can be prepared by reducing the nitro-containing compounds of the formula VIII. Reducing agents which can be used are the traditional reducing agents such as iron (Bechamps reduction), tin(II) chloride or else hydrogen with a catalyst, for example Raney nickel or palladium/charcoal. The reaction conditions correspond to those mentioned in the literature (for example Houben Weyl "Methoden der organischen Chemie" [Methods in Organic Chemistry]).

If $R_1$ is a 6-membered heterocycle, compounds of the formula VIII can be obtained from compounds of the formula IX by reacting them with suitably substituted 2-halopyridines, 2-halopyrazines, 3-halopyridazines, 2-halopyrimidines or 4-halopyrimidines (formula group X). The reaction takes place in inert organic solvents, preferably in polar solvents such as DMF, DMSO, DMA or ketones such as acetone or ethyl methyl ketone, alcohols such as ethanol, propanol, butanol, or ethers such as diethyl ether or tetrahydrofuran, in the presence of a base, preferably alkali metal (hydrogen) carbonates or hydroxides such as $Na_2CO_3$, $K_2CO_3$, NaOH or KOH or amines such as triethylamine or pyridine. The reaction temperature is between 0° C. and +150° C., preferably 80°–120° C.

Alternatively, compounds of the formula VIII are accessible by reacting compounds of the formula IX with suitably substituted pyridines, pyrimidines, pyridazines or pyrazines having a hydroxyl or mercapto group (formula group XII). The reaction proceeds preferably under the same conditions as described above.

The compounds of the formulae IX, X, XI and XII are either known from the literature or can be prepared by known methods.

Compounds of the formula II' can also be synthesised from compounds of the formula XIII by reacting them with 2-halopyridines, 2-halopyrazines, 3-halopyridazines or 2- or 4-halopyrimidines (formula group X). The reaction is carried out in inert organic solvents, preferably in polar solvents, for example DMF, DMSO, DMA or ketones such as acetone or ethyl methyl ketone, alcohols such as ethanol, propanol, butanol, or ethers such as diethyl ether or tetrahydrofuran, in the presence of a base. Examples of preferred bases are carbonates such as sodium carbonate or potassium carbonate, but also hydroxides such as potassium hydroxide or sodium hydroxide or amines such as triethylamine or pyridine. The reaction temperature is between 0° C. and 150° C., preferably 80° C. to 120° C.

Compounds of the formula XIII can be prepared from compounds of the formula XIV as described above.

Compounds of the formula XIV can be prepared by reducing the nitro group in compounds of the formula IX. Examples of reducing agents which can be used are iron (Bechamps reduction), tin(II) chloride or else hydrogen in the presence of a catalyst, for example Raney nickel or palladium-on-charcoal. The reaction conditions correspond to those indicated in the literature (for example Houben Weyl).

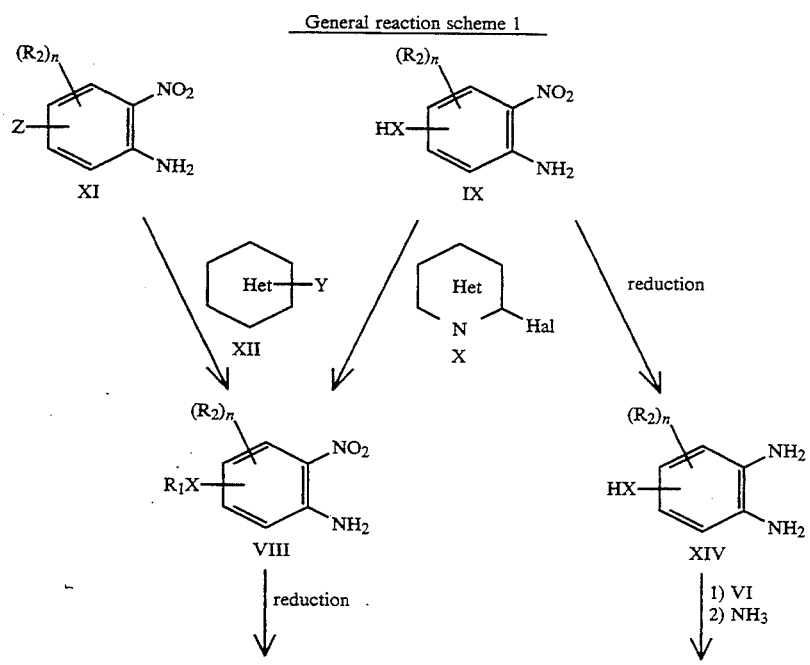

General reaction scheme 1

General reaction scheme 1

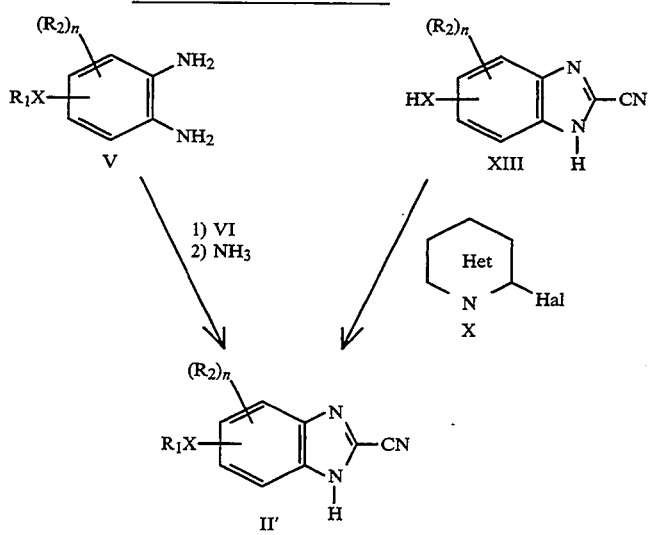

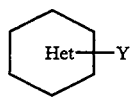

= substituted or unsubstituted hydroxypyridine, mercaptopyridine, hydroxypyrimidine, mercaptopyrimidine, hydroxypyrazine, mercaptopyrazine, hydroxypyridazine or mercaptopyridazine Z = leaving group (for example halogen) in the o- or p-position relative to the $NO_2$ group.

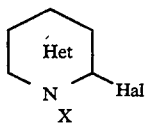

substituted or unsubstituted 2-halopyridine, -2-halopyrazine, 2- or 4-halopyrimidine, 3-halopyridazine If $R_2$ is fluorine, chlorine or bromine, then the corresponding compounds can also be obtained by halogenation of compounds in which $R_2$ is hydrogen. This applies to compounds of the formulae II', V, VII, VIII, IX, XI, XIII and XIV.

Compounds in which $R_1$ is a 5-membered heterocycle can be prepared analogously, depending on their reactivity.

If $R_1$ forms a thiazole ring, the following reaction sequence is possible:

General reaction scheme 2

Preparation of the thiazole compounds:

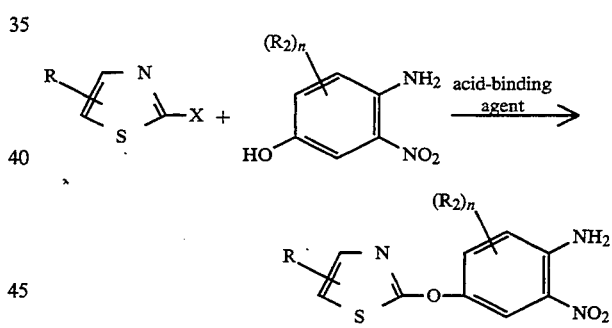

or by construction of the thiazole ring: for example

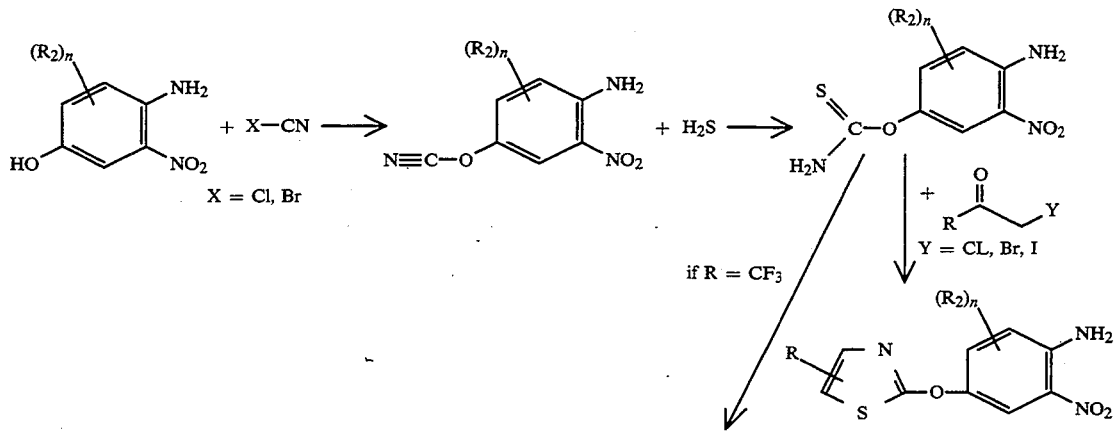

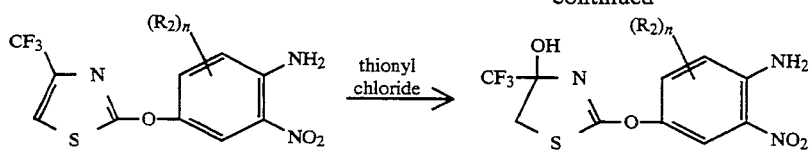 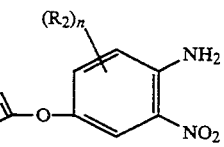

-continued

If X=S, compounds of the formula IX can also be used in a form in which they are masked as rhodanide (U.S. Pat, No. 4 076 828).

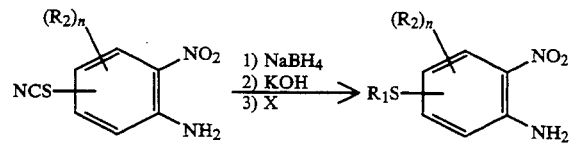

Compounds of the type

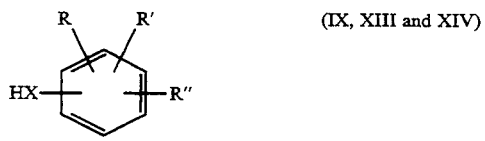

(IX, XIII and XIV)

can, if X=S, also exist in the dimeric form as the disulfide. The mercapto compounds can be obtained herefrom by reduction. Methods for such a reduction are known from the literature.

Surprisingly, it has now been found that compounds of the formula I have a biocidal spectrum for the control of phytopathogenic microorganisms, in particular fungi, which is very favourable for practical requirements. They have very advantageous curative and preventive properties and are used for the protection of a large number of crop plants. The active ingredients of the formula I allow pests which occur on plants or parts of plants (fruits, flowers, foliage, stalks, tubers, roots) of various crops of useful plants to be contained or destroyed, and even newly-forming parts of plants remain unharmed, for example by phytopathogenic fungi.

The novel active ingredients of the formula I are particularly effective against specific genera from the fungal class of the Fungi imperfecti (for example Cercospora), Basidiomycetes (for example Puccinia) as well as Ascomycetes (for example Erysiphe and Venturia) and, in particular, against Oomycetes (for example Plasmopara, Peronospora, Pythium and Phytophthora). Thus, they complement the compositions for controlling phytopathogenic fungi in crop protection in a valuable manner. As regards their use in practice, they have the advantage of having curative as well as preventive properties and can be used for the protection of a large number of crop plants. These active ingredients allow pests which occur on plants or parts of plants (fruits, flowers, foliage, stalks, tubers, roots) of various crops of useful plants to be contained or destroyed, and even newly-forming parts of plants remain unharmed, for example by phytopathogenic fungi. The compounds of the formula I can furthermore be used as seed-dressing agents for the treatment of seed (fruits, tubers, grains) and plant cuttings as a protection against fungal infections as well as against soil-borne phytopathogenic fungi.

The invention also relates to the compositions which comprise compounds of the formula I as active component, in particular crop-protecting compositions, and to their use in the agricultural sector or in related fields.

In addition, the present invention also embraces the preparation of these compositions, which comprises intimately mixing the active ingredient with one or more substances or substance groups described in this publication. It also embraces a method for treating plants, which is distinguished by application of the novel compounds of the formula I, or of the novel compositions.

Examples of plant species which are suitable as target crops for the crop-protecting use disclosed in this publication are, within the scope of this invention, the following: cereals (wheat, barley, rye, oats, rice, maize, sorghum and related species); beet (sugar beet and fodder beet); pomaceous fruit, stone fruit and soft fruit (apples, pears, plums, peaches, almonds, cherries, strawberries, raspberries and blackberries); pulses (beans, lentils, peas, soya beans); oil crops (oilseed rape, mustard, poppies, olives, sunflowers, coconut, castor-oil plants, cacao, groundnuts); curcurbits (pumpkin, cucumbers, melons); fibre plants (cotton, flax, hemp, jute); citrus fruit (oranges, lemons, grapefruit, tangerines); vegetables (spinach, lettuce, asparagus, cabbage species, carrots, onions, tomatoes, potatoes, bell peppers); Laurateac (avocado, cinnamonium, camphor) or plants such as tobacco, nuts, coffee, sugar cane, tea, pepper, grape vines, hops, Musaceae and natural latex plants, as well as ornamentals.

Active ingredients of the formula I are customarily used in the form of combinations and can be applied to the area to be treated or the plant simultaneously or in succession with other active ingredients. These other active ingredients can be fertilizers, trace element mediators or other preparations which have an effect on the growth of plants. However, selective herbicides as well as insecticides, fungicities, bactericides, nematicides, molluscicides or mixtures of a plurality of these preparations, if appropriate together with other carriers conventionally used in the art of formulation, surfactants or other application-enhancing additives, can also be used.

Suitable carder and additives can be solid or liquid and are those substances which are expedient in the an of formulation, for example natural or regenerated mineral substances, solvents, dispersants, wetting agents, adhesives, thickeners, binders or fertilizers.

A preferred process for applying an active ingredient of the formula I, or of an agrochemical composition comprising at least one of these active ingredients, is applying it to the foliage (foliar application). The frequency and rate of application depend on the risk of infestation with the pathogen in question. Compounds of the formula I can also be applied to seeds (coating) either by soaking the grains in a liquid composition of the active ingredient or coating them with a solid composition.

The compounds of the formula I are employed as pure active ingredients or, preferably, together with auxiliaries customary in the art of formulation. To this end, it is expedient to process them in a known manner to give, for example, emulsion concentrates, spreadable pastes, directly sprayable or dilutable solutions, dilute emulsions, wettable powders. soluble powders, dusts, granules, by encapsulations, for example in polymeric substances.

The application methods such as spraying, atomising, dusting, scattering, painting on or pouring, as well as the nature of the compositions, are selected to suit the intended aims and the prevailing circumstances.

Favourable application rates are generally 5 g to 2 kg of active ingredient (a.i.) per hectare (ha), preferably 10 g to 1 kg of a.i./ha, in particular 20 g to 600 g of a.i./ha.

The formulations, i.e. the compositions or combinations comprising the active ingredient of the formula I and, if desired, a solid or liquid additive, are prepared in a known manner, for example by intimately mixing and/or grinding the active ingredient with extenders such as solvents, solid carriers and, if appropriate, surface-active compounds (suffactants).

The following are possible as solvents: aromatic hydrocarbons, preferably the fractions $C_8$ to $C_{12}$, such as xylene mixture or substituted naphthalenes, phthalates such as dibutyl phthalate or dioctyl phthalate, aliphatic hydrocarbons such as cyclohexane or paraffins, alcohols and glycols as well as their ethers and esters, such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or dimethylformamide, and epoxidised or unepoxidised vegetable oils, such as epoxidised coconut oil or soya oil, and water.

Solid carriers which are generally used, for example for dusts and dispersible powders, are ground natural minerals such as calcite, talc, kaolin, montmorillonite or attapulgite. To improve the physical properties, it is also possible to add highly-disperse silica or highly-disperse adsorptive polymers. Possible particulate, adsorptive carders for granules are porous types, such as pumice, brick grit, sepiolite or bentonite, or non-sorptive carrier materials, for example calcite or sand. Moreover, a large number of pregranulated materials of inorganic or organic nature, such as dolomite or comminuted plant residues, can be used.

Suitable surface-active compounds are non-ionic, cationic and/or anionic surfactants having good emulsifying, dispersing and wetting properties, depending on the nature of the active ingredient of the formula I to be formulated. Surfactants are also to be understood as meaning mixtures of surfactants.

Suitable anionic surfactants can be either so-called water-soluble soaps or water-soluble synthetic surface-active compounds.

Examples of non-ionic surfactants which may be mentioned are nonylphenol polyethoxyethanols, castor oil polyglycol ether, polypropylene/polyethylene oxide adducts, tributylphenoxypolyethylene-ethariol, polyethylene glycol and octylphenoxypolyethoxyethanol.

Other suitable substances are fatty acid esters of polyoxyethylene sorbitan, such as polyoxyethylene sorbitan trioleate.

Cationic surfactants are mainly quaternary ammonium salts which contain, as N-substituent, at least one alkyl radical having 8 to 22 C atoms, and lower, optionally halogenated alkyl radicals, benzyl radicals or lower hydroxyalkyl radicals as further substituents.

Other surfactants conventionally used in the art of formulation are known to those skilled in the art or can be found in the specialist literature.

As a rule, the agrochemical preparations comprise 0.1 to 99 per cent by weight, in particular 0.1 to 95 per cent by weight, of active ingredient of the formula I, 99.9 to 1 per cent by weight, in particular 99.8 to 5 per cent by weight, of a solid or liquid additive and 0 to 25 per cent by weight, in particular 0.1 to 25, per cent by weight, of a surfactant.

While concentrated compositions are often preferred as commercial products, the end consumer generally uses dilute compositions.

The compositions can also comprise other additives such as stabilisers, defoamers, viscosity regulators, binders or adhesives, as well as fertilizers or other active ingredients for achieving specific effects.

The examples which follow illustrate the abovedescribed invention without imposing any limitation to the scope thereof. Temperatures are in degree centrigrade.

PREPARATION EXAMPLES

H-1. Preparation of

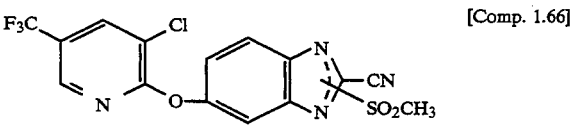

[Comp. 1.66]

1(3)-Methanesulfonyl-2-cyano-6-(3-chloro-5-trifluoromethylpyridin-2-yloxy)-benzimidazole a) Preparation of the intermediate 2-cyano-5-(3-chloro-5-trifluoromethylpyridin-2-yloxy)-benzimidazole.

4.55 g (15 mmol) of 1,2-diamino-4-(3-chloro-5-trifluoromethylpyridin-2-yloxy)benzene are dissolved in 35 ml of glacial acetic acid, and 3.95 g (22 mmol) of methyl 2,2,2-trichloroacetimidate are added dropwise with stirring at room temperature. Stirring is continued for 14 hours, the mixture is poured into 150 ml of water and extracted three times using in each case 40 ml of ethyl ether, the combined extracts are dried over sodium sulfate, and the solvent is evaporated. The resulting 2-trichloromethyl-5-(3-chloro-5-trifluoromethylpyridin-2-yloxy)-benzimidazole, in the form of a dark brown oil, is dissolved without further purification in 30 ml of tetrahydrofuran, 70 ml of a 25% aqueous ammonia solution are added in the course of 1 hour at room temperature, with stirring, and stirring is continued for 1 hour. After the tetrahydrofuran has been distilled off in vacuo, the mixture is brought to a pH of 5 using concentrated hydrochloric acid, and the solid which has precipitated is filtered off with suction and chromatographed over a silica gel column using ethyl acetate/hexane (1:1). After evaporation of the eluent, the crystalline precipitate is digested with 15 ml of hexane, filtered and dried. The beige crystals melt >270° C.

b) Preparation of the end product 1.02 g (15.5 mmol) of 85% potassium hydroxide are added in one portion to a solution of 4.14 g ( 12 mmol) of 2-cyano-5-(3-chloro-5-trifluoromethylpyridin-2-yloxy)-benzimidazole in 65 ml of acetone, and the mixture is stirred for one hour. 3.2 g (28 mmol) of methanesulfonyl chloride are added dropwise in the course of one hour at room temperature to this mixture, and stirring is continued for 16 hours at 20° C. To complete the reaction, a further 0.5 g (7.6 mmol) of 85% potassium hydroxide and, after half an hour, 1.6 g (14 mmol) of methanesulfonyl chloride are added, and stirring is continued for four hours at room temperature. The reaction mixture is subsequently poured into 200 ml of water and extracted three times using in each case 30 ml of ethyl acetate, the combined organic phases are washed twice using in each case 20 ml of saturated aqueous sodium carbonate solution and once using 20 ml of water, dried over sodium sulfate and filtered. The solvent is then evaporated. The bulk of crystals is digested using 20 ml of diethyl ether, filtered and dried. The pale grey crystals melt at 196°–206° C.

H-2. Preparation of

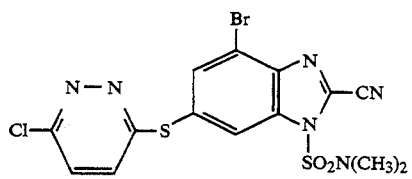

[Comp. 1.304]

1-N,N-Dimethylsulfamoyl-2-cyano-4-bromo-6-(6-chloro-pyridazin-3-ylthio)-benzimidazole a) Preparation of the intermediate 2-nitro-4-(6-chloro-pyridazin-3-ylthio)aniline.

78.1 g of 2-nitro-4-rhodano-aniline are dissolved in 900 ml of diglyme at 30° .C and successively treated with 15.2 g of sodium borohydride. After the mixture has been stirred for 1 hour at 60° C., it is cooled to room temperature, and 26.4 g of pulverised potassium hydroxide and 61.4 g of 3,6-dichloropyridazine are added. After the mixture has been stirred for 1 hour at 60° C., it is poured onto ice, and the suspension is filtered. Recrystallisation from toluene and digestion with diethyl ether give 39.4 g of product a), m.p.>230° C.

b) Preparation of the intermediate 2-bromo-4-(6-chloro-pyridazin-3-ylthio)-6-nitro-aniline.

10.0 g of the compound a) and 2.9 g of sodium acetate are dissolved in 130 ml of glacial acetic acid. 7.5 g of bromine are slowly added dropwise, and the suspension is stirred for 30 minutes at 55° C. The mixture is poured onto ice and filtered, and the solid is washed with water and dried. Chromatography on silica gel using ethyl acetate:hexane=1:1 as the eluent gives 6.4 g of compound b), m.p.>250° C.

c) Preparation of the intermediate 1,2-diamino-3-bromo-5-(6-chloro-pyridazin-3-ylthio)benzene.

6.4 g of compound b) are dissolved in 200 ml of tetrahydrofuran, 1.2 g of Raney nickel are added, and the mixture is stirred for 51 hours at room temperature under a hydrogen atmosphere. A total of 3.6 g of Raney nickel is added in two portions. The catalyst is subsequently filtered off, and the solvent is evaporated. 4.3 g of compound c), m.p. 160°–161° C., are obtained.

d) Preparation of the intermediate 2-cyano-4-bromo-6-(6-chloro-pyridazin-3-ylthio)-benzimidazole.

4.3 g of compound c) are suspended in 30 ml of glacial acetic acid. 3.55 g of methyl 2,2,2-trichloroacetimidate are added dropwise, and the mixture is stirred for 1 hour at room temperature. The mixture is poured into ice-water and extracted three times using in each case 20 ml of diethyl ether. The organic phase is dried over sodium sulfate, filtered and concentrated. The residue is dissolved in 30 ml of tetrahydrofuran, and the solution is added dropwise at room temperature to 60 ml of concentrated ammonia solution. After 1 hour, the reaction mixture is concentrated, diluted with water and acidified with concentrated HCl solution. The suspension formed is filtered, washed with water and dried. 4.6 g of compound d), m.p.>250° C., are obtained.

e) Preparation of the end product 2.3 g of compound d) are dissolved in 10 ml of N-methyl-2-pyrrolidone, and 0.28 g of 60% sodium hydride are added. When the evolution of gas has ceased, stirring is continued for 10 minutes at 40° C., and the mixture is cooled to 15° C. 0.876 ml of N,N-dimethylsulfamic acid chloride are added. The dark brown suspension is stirred for 60 minutes at room temperature and for 30 minutes at 35° C. The mixture is poured into ice-water and extracted three times using in each case 20 ml of ethyl acetate. The organic phases are washed with water and saline, dried over sodium sulfate, filtered and concentrated. The residue is chromatographed on silica gel using ethyl acetate:hexane=1:1.1.17 g of the title compound are obtained, m.p. 169°–170° C.

H-3. Preparation of

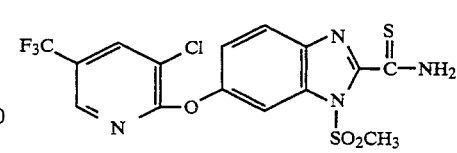

[Comp. 3.34]

1(3)-Methanesulfonyl-2-thioamido-6-(3-chloro-5-trifluoromethyl-pyridin-2-yloxy)-benzimidazole 1.12 g of compound No. 1.66 are dissolved in 12 ml of dioxane and 4 ml of tetrahydrofuran. 0.43 ml of triethylamine are added, and hydrogen sulfide is passed in for 30 minutes at room temperature. The solution is concentrated to half its volume and poured into ice-water. The mixture is extracted using ethyl acetate. The organic phase is washed with saline, dried over sodium sulfate, filtered and concentrated. The crystals which form are digested with ether. 0.47 g of compound No. 3.34, m.p. 181°–182° C. result.

H-4. Preparation of

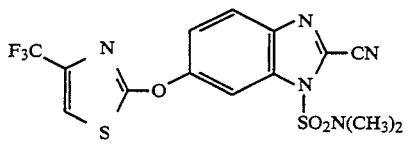

[Comp. 1.250]

1(3)-N,N-Dimethylsulfamoyl-2-cyano-6-(4-trifluoromethyl-2-oxo-thiazolyl)-benzimidazole This product was prepared by the method already described under H-2 from the following intermediate:

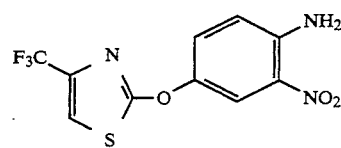

Preparation of the intermediate 50.0 g of 4-amino-3-nitrophenol are dissolved in 40 ml of acetone, and 34.4 g of cyanogen bromide am subsequently added. 32.9 g of triethylamine are added dropwise at 0°–5° C. in the course of 45 minutes. Towards the end of the addition of the triethylamine, a further 100 ml of acetone are added. Stirring is subsequently continued for 15 minutes. The reaction mixture is filtered through Hyflo, washed with acetone and concentrated. 64.7 g of an orange-yellow powder are obtained, and this is used directly in the next step. The product is dissolved in 500 ml of tetrahydrofuran and the solution is refiltered to remove traces of triethylamine salts. 12.0 g of hydrogen sulfide are subsequently passed in in the course of 3 hours at 25°–30° C., and stirring is continued for a further hour. For work-up, the reaction mixture is poured into ice/water, with stirring, filtered and washed with water. The moist solid is dissolved in ethyl acetate, water is removed from the mixture using magnesium sulfate, and the mixture is filtered and concentrated. 56.0 g of 4-amino-3-nitrophenyl thiocarbamate are obtained as an orange powder. 1.0 g of this aminonitrophenyl thiocarbamate are dissolved in 10 ml of dioxane/toluene (1:1), and 1.2 g of bromotrifluoroacetone are added dropwise. The reaction mixture is stirred for 1 hour at 35° C. and then filtered, washed with hexane and ether and dried. To eliminate water, this powder is suspended in dichloroethane and refluxed for one hour together with 2.5 g of thionyl chloride. The reaction mixture is concentrated, the residue is taken up in ethyl acetate, the mixture is washed with 10% potassium carbonate solution and saline, and the organic phase is dried over magnesium sulfate and concentrated. 0.35 g of an orange oil of 1-amino-2-nitro-4-(4-trifluoromethyl-2-oxo-thiazolyl)-benzene, which is pure according to $^1$H NMR spectrum, are obtained, and this is processed directly to give the end product.

Reaction scheme for the preparation of the intermediate:

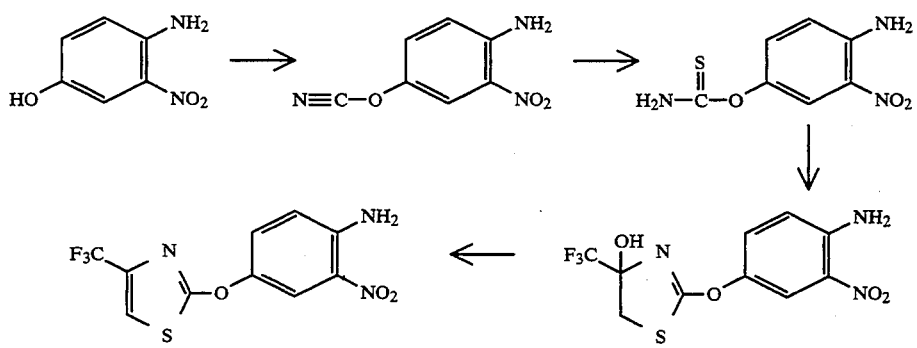

Examples of compounds which can be prepared in this manner or following one of the methods indicated further above are the following.

TABLE 1

Compounds of the formula

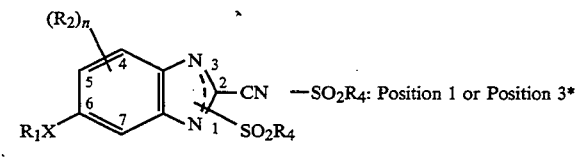

—SO$_2$R$_4$: Position 1 or Position 3*

| Comp. No. | R$_1$X | (R$_2$)$_n$ | R$_4$ | Physical data |
|---|---|---|---|---|
| 1.1 | (2-pyridyloxy) | H | —CH$_3$ | |
| 1.2 | (5-trifluoromethyl-2-pyridyloxy) | H | —CH$_3$ | m.p. 176–181° C. |
| 1.3 | (3,5-dichloro-2-pyridyloxy) | H | —CH$_3$ | m.p. 202–204° C. |
| 1.4 | (2-pyridyloxy) | H | —N(CH$_3$)$_2$ | |

TABLE 1-continued

Compounds of the formula

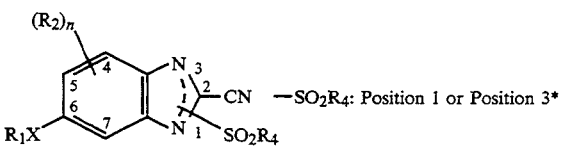
—SO₂R₄: Position 1 or Position 3*

| Comp. No. | R₁X | (R₂)ₙ | R₄ | Physical data |
|---|---|---|---|---|
| 1.5 | (2-pyridyloxy) | 5-F | —CH₃ | |
| 1.6 | (2-pyridyloxy) | 5-Cl | —CH₃ | |
| 1.7 | (5-CF₃-2-pyridyloxy) | H | —C₃H₇-n | m.p. 168–171° C. |
| 1.8 | (3,5-dichloro-2-pyridyloxy) | H | —C₃H₇-n | m.p. 166–170° C. |
| 1.9 | (5-CF₃-2-pyridyloxy) | 4-Cl | —CH₃ | m.p. 203–205° C. |
| 1.10 | (2-pyridyloxy) | H | —N(CH₃)₂ | m.p. 145–146° C. |
| 1.11 | (2-pyridyloxy) | 5-Br | —CH₃ | |
| 1.12 | (3,5-dichloro-2-pyridyloxy) | H | —N(CH₃)₂ | m.p. 134–135° C. |
| 1.13 | (5-CF₃-2-pyridyloxy) | 5-Cl | —CH₃ | m.p. 202–205° C. |
| 1.14 | (5-CF₃-2-pyridyloxy) | 4-Br | —CH₃ | m.p. 213–214° C. |
| 1.15 | (3,5-dichloro-2-pyridyloxy) | 4-Cl | —CH₃ | |

TABLE 1-continued
Compounds of the formula
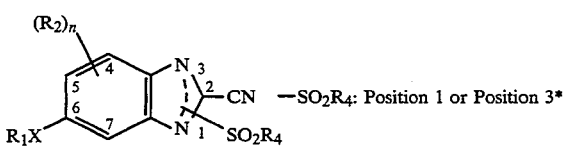
—SO₂R₄: Position 1 or Position 3*
| Comp. No. | R₁X | (R₂)ₙ | R₄ | Physical data |
|---|---|---|---|---|
| 1.16 | 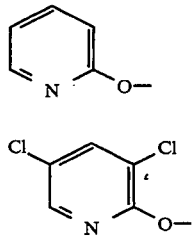 | 5-Br | —N(CH₃)₂ | |
| 1.17 | 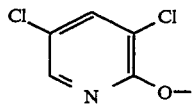 | 4-Br | —CH₃ | m.p. 209–210° C. |
| 1.18 | 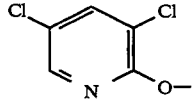 | 5-Cl | —CH₃ | m.p. 185–187° C. |
| 1.19 | 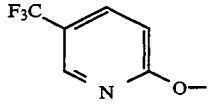 | 4-Br | —C₃H₇-n | m.p. 139–140.5° C. |
| 1.20 | 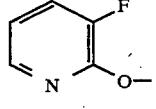 | 4-Br | —C₃H₇-n | m.p. 164–166° C. |
| 1.21 | 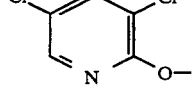 | 4-CF₃ | —CH₃ | |
| 1.22 | 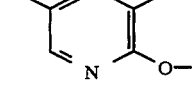 | 5-Cl | —N(CH₃)₂ | m.p. 170–190° C. |
| 1.23 | 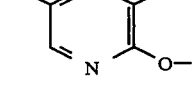 | 4-Br | —N(CH₃)₂ | m.p. 156–172° C. |
| 1.24 | 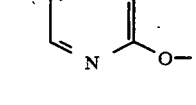 | H | —CH₃ | m.p. 196–199° C. |
| 1.25 | 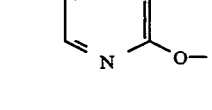 | 4-Br | —CH₃ | m.p. 219–220.5° C. |
| 1.26 |  | 4-Br | —N(CH₃)₂ | m.p. 160–162° C. |

TABLE 1-continued

Compounds of the formula

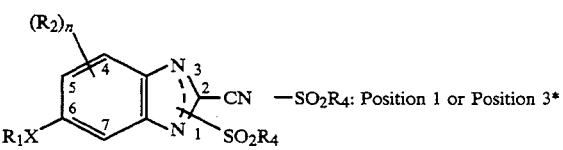

—SO$_2$R$_4$: Position 1 or Position 3*

| Comp. No. | R$_1$X | (R$_2$)$_n$ | R$_4$ | Physical data |
|---|---|---|---|---|
| 1.27 | 2-pyridyloxy | 4-CF$_3$ | —CH$_3$ | |
| 1.28 | 5-CF$_3$-2-pyridyloxy | 5-Br | —CH$_3$ | |
| 1.29 | 5-Cl-2-pyridyloxy | H | —CH$_3$ | m.p. 145–146° C. |
| 1.30 | 3,5-diCl-2-pyridyloxy | 5-Br | —CH$_3$ | |
| 1.31 | 5-Cl-3-F-2-pyridyloxy | H | —C$_3$H$_7$-n | m.p. 143–147° C. |
| 1.32 | 3,5-diCl-2-pyridyloxy | 5-Br | —N(CH$_3$)$_2$ | |
| 1.33 | 5-Cl-2-pyridyloxy | H | —N(CH$_3$)$_2$ | |
| 1.34 | 5-Cl-2-pyridyloxy | 5-F | —CH$_3$ | |
| 1.35 | 3,5-diCl-2-pyridyloxy | 5-CH$_3$ | —CH$_3$ | |
| 1.36 | 5-CF$_3$-2-pyridyloxy | 5-Br | —N(CH$_3$)$_2$ | |
| 1.37 | 5-Cl-2-pyridyloxy | 5-Cl | —CH$_3$ | |

TABLE 1-continued

Compounds of the formula (R₂)ₙ on benzimidazole (positions 4-7), N3, C2-CN, N1-SO₂R₄: Position 1 or Position 3*

| Comp. No. | R₁X | (R₂)ₙ | R₄ | Physical data |
|---|---|---|---|---|
| 1.38 | 5-Cl, 3-F pyridin-2-yl-O— | H | —N(CH₃)₂ | m.p. 136–139° C. |
| 1.39 | 5-CF₃ pyridin-2-yl-O— | 5-CH₃ | —CH₃ | |
| 1.40 | 3,5-diCl pyridin-2-yl-O— | 5-OCH₃ | —CH₃ | |
| 1.41 | 3,5-diCl pyridin-2-yl-O— | 4-CF₃ | —CH₃ | |
| 1.42 | 5-Cl pyridin-2-yl-O— | 5-Br | —CH₃ | |
| 1.43 | 5-CF₃ pyridin-2-yl-O— | 5-OCH₃ | —CH₃ | |
| 1.44 | 5-Cl, 3-F pyridin-2-yl-O— | 4-Cl | —CH₃ | |
| 1.45 | 5-Cl, 3-F pyridin-2-yl-O— | 4-Br | —C₃H₇-n | m.p. 177–178° C. |
| 1.46 | 5-Cl pyridin-2-yl-O— | 5-Br | —N(CH₃)₂ | |
| 1.47 | 5-CF₃ pyridin-2-yl-O— | 5-OCH₃ | —N(CH₃)₂ | |
| 1.48 | 5-Cl pyridin-2-yl-O— | 5-OCHF₂ | —CH₃ | |

TABLE 1-continued

Compounds of the formula

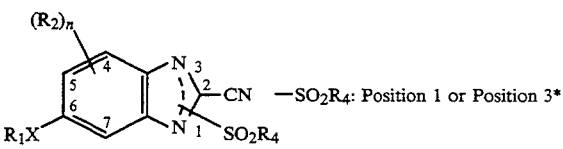

—SO₂R₄: Position 1 or Position 3*

| Comp. No. | R₁X | (R₂)ₙ | R₄ | Physical data |
|---|---|---|---|---|
| 1.49 | 3,5-dichloro-2-pyridyloxy | 5-CF₃ | —CH₃ | |
| 1.50 | 5-trifluoromethyl-2-pyridyloxy | 4-CF₃ | —CH₃ | |
| 1.51 | 5-chloro-3-fluoro-2-pyridyloxy | 4-Cl | —N(CH₃)₂ | |
| 1.52 | 5-chloro-2-pyridyloxy | 5-CF₃ | —CH₃ | |
| 1.53 | 5-chloro-3-fluoro-2-pyridyloxy | 5-Cl | —CH₃ | m.p. 189–193° C. |
| 1.54 | 5-chloro-3-fluoro-2-pyridyloxy | 4-Br | —N(CH₃)₂ | m.p. 174–176° C. |
| 1.55 | 5-bromo-2-pyridyloxy | H | —CH₃ | m.p. 179–180° C. |
| 1.56 | 5-trifluoromethyl-2-pyridyloxy | 4-CF₃ | —N(CH₃)₂ | |
| 1.57 | 3,5-dichloro-2-pyridyloxy | 5-CF₃ | —N(CH₃)₂ | |
| 1.58 | 6-methoxy-2-pyridyloxy | H | —CH₃ | |
| 1.59 | 5-chloro-3-fluoro-2-pyridyloxy | 5-Cl | —N(CH₃)₂ | m.p. 128–132° C. |

TABLE 1-continued
Compounds of the formula
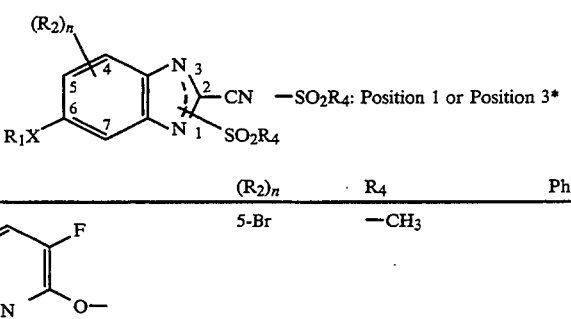
—SO$_2$R$_4$: Position 1 or Position 3*
| Comp. No. | R$_1$X | (R$_2$)$_n$ | R$_4$ | Physical data |
|---|---|---|---|---|
| 1.60 | 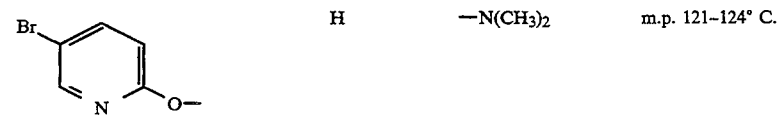 | 5-Br | —CH$_3$ | |
| 1.61 |  | H | —N(CH$_3$)$_2$ | m.p. 121–124° C. |
| 1.62 |  | 5-CF$_3$ | —CH$_3$ | |
| 1.63 | 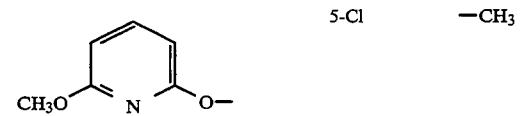 | 5-Cl | —CH$_3$ | |
| 1.64 |  | 5-Cl | —CH$_3$ | |
| 1.65 | 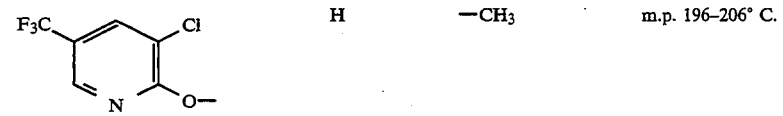 | 4-CF$_3$ | —CH$_3$ | |
| 1.66 |  | H | —CH$_3$ | m.p. 196–206° C. |
| 1.67 | 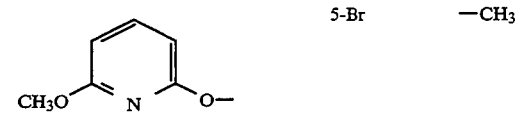 | 5-Br | —CH$_3$ | |
| 1.68 |  | 5-Br | —CH$_3$ | |
| 1.69 | | 4-CF$_3$ | —CH$_3$ | |
| 1.70 |  | 5-CF$_3$ | —CH$_3$ | |

TABLE 1-continued

Compounds of the formula

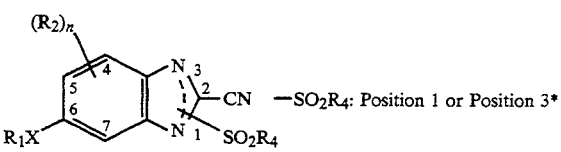
—SO$_2$R$_4$: Position 1 or Position 3*

| Comp. No. | R$_1$X | (R$_2$)$_n$ | R$_4$ | Physical data |
|---|---|---|---|---|
| 1.71 | 5-CF$_3$-pyridin-2-yl-O— | 5-CF$_3$ | —N(CH$_3$)$_2$ | |
| 1.72 | 3,5-di(CH$_3$O)-pyridin-2-yl-O— | 5-CF$_3$ | —CH$_3$ | |
| 1.73 | 3-Cl-5-CF$_3$-pyridin-2-yl-O— | H | —C$_2$H$_5$ | |
| 1.74 | 3-Cl-5-CF$_3$-pyridin-2-yl-O— | H | cyclopropyl | |
| 1.75 | 5-Cl-3-F-pyridin-2-yl-O— | 5-CF$_3$ | —N(CH$_3$)$_2$ | |
| 1.76 | 5-Br-pyridin-2-yl-O— | 5-CF$_3$ | —CH$_3$ | |
| 1.77 | 3-Cl-5-CF$_3$-pyridin-2-yl-O— | H | —C$_3$H$_7$-n | m.p. 130–132° C. |
| 1.78 | 3-Cl-5-CF$_3$-pyridin-2-yl-O— | H | cyclopentyl | |
| 1.79 | 3-Cl-5-CF$_3$-pyridin-2-yl-O— | 5-OCH$_3$ | —CH$_3$ | m.p. 201–203° C. |
| 1.80 | 3-Cl-5-CF$_3$-pyridin-2-yl-O— | 4-CF$_3$ | —CH$_3$ | |
| 1.81 | 3-Cl-5-CF$_3$-pyridin-2-yl-O— | 4-Cl, 5-Cl | —CH$_3$ | |

TABLE 1-continued

Compounds of the formula

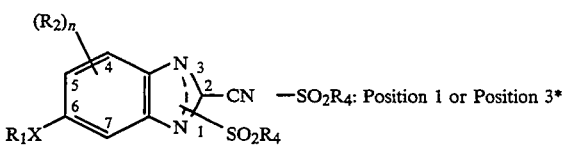

—SO₂R₄: Position 1 or Position 3*

| Comp. No. | R₁X | (R₂)ₙ | R₄ | Physical data |
|---|---|---|---|---|
| 1.82 | F₃C-[3-Cl-pyridin-2-yl-O]- | H | —N(CH₃)₂ | m.p. 175–176° C. |
| 1.83 | F₃C-[3-Cl-pyridin-2-yl-O]- | H | —N(C₂H₅)₂ | |
| 1.84 | O₂N-[pyridin-2-yl-O]- | H | —CH₃ | |
| 1.85 | F₃C-[3-Cl-pyridin-2-yl-O]- | 5-OCH₃ | —N(CH₃)₂ | |
| 1.86 | [pyridin-2-yl-S]- | 5-Br | —CH₃ | |
| 1.87 | F₃C-[3-Cl-pyridin-2-yl-O]- | H | —N(CH₃)(C₂H₅) | |
| 1.88 | F₃C-[3-Cl-pyridin-2-yl-O]- | 4-OCHF₂ | —CH₃ | |
| 1.89 | [pyridin-2-yl-S]- | H | —CH₃ | m.p. 157–160° C. |
| 1.90 | F₃C-[3-Cl-pyridin-2-yl-O]- | H | cyclohexyl | |
| 1.91 | F₃C-[3-Cl-pyridin-2-yl-O]- | 5-OCHF₂ | —CH₃ | |
| 1.92 | F₃C-[3-Cl-pyridin-2-yl-O]- | 5-Br | —CH₃ | m.p. 201–205° C. |

TABLE 1-continued
Compounds of the formula
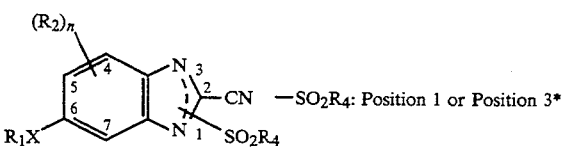
—SO₂R₄: Position 1 or Position 3*
| Comp. No. | R₁X | (R₂)ₙ | R₄ | Physical data |
|---|---|---|---|---|
| 1.93 | O₂N—pyridyl-O— (5-nitro-2-pyridyloxy) | 5-Cl | —CH₃ | |
| 1.94 | F₃C, Cl-pyridyl-O— | 4-F | —CH₃ | |
| 1.95 | F₃C, Cl-pyridyl-O— | 4-CF₃ | —N(CH₃)₂ | |
| 1.96 | pyridyl-S— | H | —N(CH₃)₂ | m.p. 137–138° C. |
| 1.97 | F₃C, Cl-pyridyl-O— | 4-F | —CH₃ | |
| 1.98 | F₃C, Cl-pyridyl-O— | 4-OCF₃ | —CH₃ | |
| 1.99 | pyridyl-S— | 5-Cl | —CH₃ | m.p. 170–171° C. |
| 1.100 | pyridyl-S— | 5-CF₃ | —CH₃ | |
| 1.101 | F₃C, Cl-pyridyl-O— | 5-F | —CH₃ | |
| 1.102 | pyridyl-S— | 5-CF₃ | —N(CH₃)₂ | |
| 1.103 | F₃C, Cl-pyridyl-O— | 5-F | —N(CH₃)₂ | |

TABLE 1-continued
Compounds of the formula
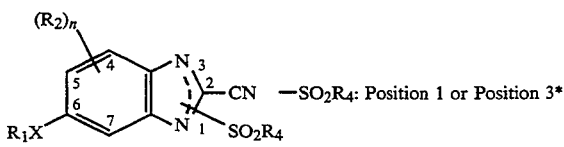
—SO₂R₄: Position 1 or Position 3*
| Comp. No. | R₁X | (R₂)ₙ | R₄ | Physical data |
|---|---|---|---|---|
| 1.104 | F₃C-, Cl, pyridyl-O— | 4-Cl | —CH₃ | m.p. 206–209° C. |
| 1.105 | F₃C-, Cl, pyridyl-O— | 5-OCF₃ | —CH₃ | |
| 1.106 | F₃C-, Cl, pyridyl-O— | 5-CF₃ | —CH₃ | |
| 1.107 | F₃C-, Cl, pyridyl-O— | 5-Cl | —CH₃ | m.p. 194–225° C. |
| 1.108 | pyridyl-S— | H | —CH₃ | |
| 1.109 | F₃C-, Cl, pyridyl-O— | 5-Br | —N(CH₃)₂ | m.p. 188–192° C. |
| 1.110 | pyrimidinyl-S— | H | —CH₃ | |
| 1.111 | F₃C-, Cl, pyridyl-O— | 5-Cl | —C₂H₅ | |
| 1.112 | thiazolyl-S— | H | —CH₃ | |
| 1.113 | F₃C-, Cl, pyridyl-O— | 5-Br | cyclopentyl | |
| 1.114 | pyridyl-S— | H | —N(CH₃)₂ | m.p. 113–115° C. |

TABLE 1-continued

Compounds of the formula

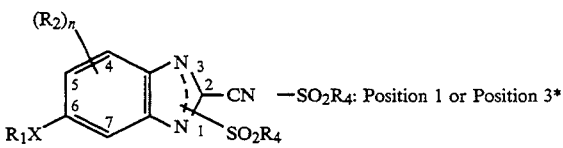
—SO₂R₄: Position 1 or Position 3*

| Comp. No. | R₁X | (R₂)ₙ | R₄ | Physical data |
|---|---|---|---|---|
| 1.115 | F₃C-, Cl, pyridine-O– | 5-Cl | —N(CH₃)₂ | m.p. 199–232° C. |
| 1.116 | pyrimidine-S– | H | —N(CH₃)₂ | |
| 1.117 | F₃C-, Cl, pyridine-O– | 5-OCF₃ | —N(CH₃)₂ | |
| 1.118 | F₃C-, Cl, pyridine-O– | 5-Cl | cyclopropyl | |
| 1.119 | O₂N-, pyridine-O– | 5-CF₃ | H | |
| 1.120 | thiazole-S– | H | —N(CH₃)₂ | |
| 1.121 | O₂N-, thiazole-O– | H | —CH₃ | |
| 1.122 | F₃C-, Cl, pyridine-O– | 5-Cl | cyclopentyl | |
| 1.123 | pyrazine-O– | H | —CH₃ | |
| 1.124 | thiazole-O– | H | —CH₃ | m.p. 103–105° C. |
| 1.125 | pyrazine-O– | 5-Cl | —CH₃ | |
| 1.126 | thiazole-O– | H | —N(CH₃)₂ | |

TABLE 1-continued

Compounds of the formula

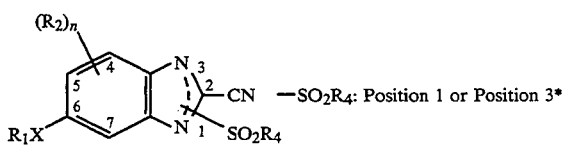

—SO₂R₄: Position 1 or Position 3*

| Comp. No. | R₁X | (R₂)ₙ | R₄ | Physical data |
|---|---|---|---|---|
| 1.127 | F₃C-, Cl-pyridinyl-O— | 5-Cl | cyclohexyl | |
| 1.128 | O₂N-thiazolyl-O— | H | —N(CH₃)₂ | |
| 1.129 | F₃C-, Cl-pyridinyl-O— | 5-CF₃ | —N(CH₃)₂ | m.p. 108–111° C. |
| 1.130 | thiazolyl-O— | 5-Cl | —CH₃ | |
| 1.131 | thienyl-O— | 5-CF₃ | —CH₃ | |
| 1.132 | pyrazinyl-O— | 5-CF₃ | —CH₃ | |
| 1.133 | F₃C-, Cl-pyridinyl-O— | 7-Cl | —CH₃ | |
| 1.134 | thiazolyl-O— | 5-Cl | —N(CH₃)₂ | |
| 1.135 | thienyl-O— | 5-Br | —CH₃ | |
| 1.136 | F₃C-, Cl-pyridinyl-O— | 4-Br | —CH₃ | m.p. 209–211.5° C. |
| 1.137 | thienyl-O— | 5-OCH₃ | —CH₃ | |
| 1.138 | F₃C-, Cl-pyridinyl-O— | 5-CF₃ | cyclopentyl | |

TABLE 1-continued
Compounds of the formula
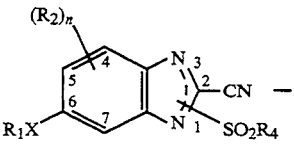
| Comp. No. | R₁X | (R₂)ₙ | R₄ | Physical data |
|---|---|---|---|---|
| 1.139 | 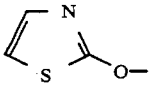 | 4-Br | —C₃H₇-n | m.p. 167–168° C. |
| 1.140 | 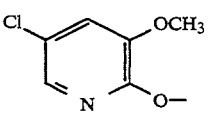 | 5-Br | —CH₃ | |
| 1.141 | 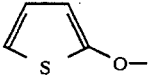 | H | —CH₃ | |
| 1.142 | 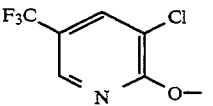 | 5-Cl | —CH₃ | |
| 1.143 | 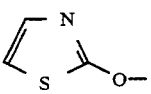 | 5-Br | cyclohexyl | |
| 1.144 | 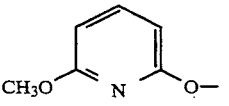 | 5-CF₃ | —CH₃ | |
| 1.145 | 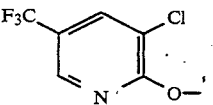 | 5-CF₃ | —CH₃ | |
| 1.146 | 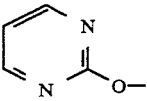 | 4-Br | —N(CH₃)₂ | m.p. 182–183° C. |
| 1.147 | 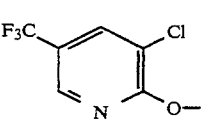 | 5-CF₃ | —CH₃ | |
| 1.148 | 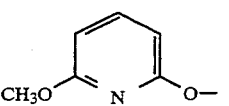 | 5-CF₃ | cyclohexyl | |
| 1.149 | 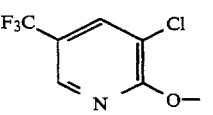 | 5-CH₃ | —CH₃ | |
| 1.150 |  | 7-Br | —CH₃ | |

TABLE 1-continued

Compounds of the formula

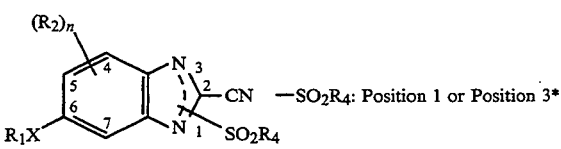

—SO$_2$R$_4$: Position 1 or Position 3*

| Comp. No. | R$_1$X | (R$_2$)$_n$ | R$_4$ | Physical data |
|---|---|---|---|---|
| 1.151 | ![CH3, CH3 pyrimidine-O-] | H | —CH$_3$ | m.p. 197–198° C. |
| 1.152 | ![F3C, Cl pyridine-O-] | 4-F, 5-Cl | —CH$_3$ | |
| 1.153 | ![F3C, Cl pyridine-O-] | 7-Br | —N(CH$_3$)$_2$ | |
| 1.154 | ![pyrimidine-O-] | H | —CH$_3$ | |
| 1.155 | ![F3C, Cl pyridine-O-] | 4-Cl, 5-CF$_3$ | —CH$_3$ | |
| 1.156 | ![F3C, Cl pyridine-O-] | 4-CH$_3$ | —CH$_3$ | |
| 1.157 | ![CH3 pyridine-O-] | 5-Br | —CH$_3$ | |
| 1.158 | ![F3C, Cl pyridine-O-] | 7-CF$_3$ | —CH$_3$ | |
| 1.159 | ![CH3, CH3 pyrimidine-O-] | H | —N(CH$_3$)$_2$ | |
| 1.160 | ![F3C, Cl pyridine-O-] | 5-CH$_3$ | —CH$_3$ | m.p. 197–202° C. |
| 1.161 | ![thiazole-O-] | 5-CF$_3$ | —N(CH$_3$)$_2$ | |

TABLE 1-continued

Compounds of the formula

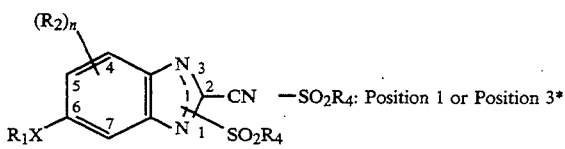
—SO$_2$R$_4$: Position 1 or Position 3*

| Comp. No. | R$_1$X | (R$_2$)$_n$ | R$_4$ | Physical data |
|---|---|---|---|---|
| 1.162 | 3-Cl, 5-CF$_3$-pyridin-2-yl-O— | 7-CF$_3$ | —N(CH$_3$)$_2$ | |
| 1.163 | 5-Cl, 3-OCH$_3$-pyridin-2-yl-O— | 5-CF$_3$ | —CH$_3$ | |
| 1.164 | 5-Cl, 3-OCH$_3$-pyridin-2-yl-O— | H | —N(CH$_3$)$_2$ | |
| 1.165 | pyrimidin-2-yl-O— | H | —CH$_3$ | |
| 1.166 | thien-2-yl-O— | H | —N(CH$_3$)$_2$ | |
| 1.167 | 3-Cl, 5-CF$_3$-pyridin-2-yl-O— | 5-CH$_3$ | —N(CH$_3$)$_2$ | m.p. 122–123° C. |
| 1.168 | 6-CH$_3$-pyridin-2-yl-O— | H | —CH$_3$ | |
| 1.169 | 5-Cl, 3-OCH$_3$-pyridin-2-yl-O— | 5-Cl | —CH$_3$ | |
| 1.170 | 3-Cl, 5-CF$_3$-pyridin-2-yl-O— | 4-OCH$_3$ | —CH$_3$ | |
| 1.171 | thien-2-yl-O— | H | —CH$_3$ | |
| 1.172 | 5-Cl, 3-OCH$_3$-pyridin-2-yl-O— | 5-Br | —CH$_3$ | |

TABLE 1-continued

Compounds of the formula

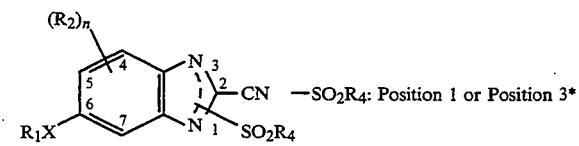

—SO₂R₄: Position 1 or Position 3*

| Comp. No. | R₁X | (R₂)ₙ | R₄ | Physical data |
|---|---|---|---|---|
| 1.173 | CH₃–pyridine–O— | H | —N(CH₃)₂ | |
| 1.174 | CH₃O–pyridine–S— | 4-Br | —CH₃ | |
| 1.175 | Cl-pyridine-S— | H | —CH₃ | |
| 1.176 | Cl-pyridine-S— | 4-Cl | —N(CH₃)₂ | |
| 1.177 | F₃C–Cl-pyridine–S— | H | —CH₃ | m.p. 174–176° C. |
| 1.178 | F₃C–Cl-pyridine–S— | 5-Cl | —CH₃ | m.p. 198–202° C. |
| 1.179 | F₃C–Cl-pyridine–S— | H | —N(CH₃)₂ | m.p. 155–156° C. |
| 1.180 | F₃C–Cl-pyridine–S— | 5-Cl | —N(CH₃)₂ | m.p. 142–145° C. |
| 1.181 | F₃C–Cl-pyridine–S— | 4-Br | —CH₃ | m.p. 238–240° C. |
| 1.182 | F₃C–Cl-pyridine–S— | 4-Cl | —N(CH₃)₂ | m.p. 192–193° C. |
| 1.183 | F₃C-pyridine-S— | 5-Cl | —CH₃ | m.p. 217–219° C. |

TABLE 1-continued
Compounds of the formula
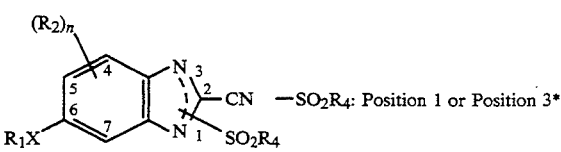
—SO₂R₄: Position 1 or Position 3*
| Comp. No. | R₁X | (R₂)ₙ | R₄ | Physical data |
|---|---|---|---|---|
| 1.184 | F₃C-pyridyl-S— | 5-Cl | —N(CH₃)₂ | m.p. 154–156° C. |
| 1.185 | 3,5-Cl₂-pyridyl-S— | 5-OCH₃ | —N(CH₃)₂ | |
| 1.186 | 3,5-Cl₂-pyridyl-S— | H | —CH₃ | |
| 1.187 | 4,6-(CH₃)₂-pyrimidyl-S— | 5-Cl | —CH₃ | m.p. 195–196.5° C. |
| 1.188 | 4,6-(CH₃O)₂-pyrimidyl-S— | H | —CH₃ | m.p. 163–165° C. |
| 1.189 | 4,6-(CH₃)₂-pyrimidyl-S— | 5-Br | —N(CH₃)₂ | |
| 1.190 | 4,6-(CH₃O)₂-pyrimidyl-S— | 4-Br | —CH₃ | |
| 1.191 | 4-CH₃O-pyrimidyl-S— | 5-OMe | —N(CH₃)₂ | |
| 1.192 | pyrazinyl-S— | 4-CF₃ | CH₃ | |

TABLE 1-continued

Compounds of the formula

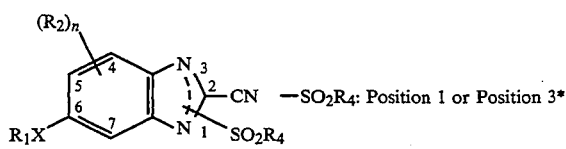

—SO$_2$R$_4$: Position 1 or Position 3*

| Comp. No. | R$_1$X | (R$_2$)$_n$ | R$_4$ | Physical data |
|---|---|---|---|---|
| 1.193 | 3-chloro-2-(thio)pyrazine | H | —CH$_3$ | |
| 1.194 | 3,6-dimethyl-2-(thio)pyrazine | 5-Cl | —N(CH$_3$)$_2$ | |
| 1.195 | 5-chloro-2-(thio)pyrazine | 5-Cl | —N(CH$_3$)$_2$ | |
| 1.196 | 5-bromo-2-(oxy)pyridine | H | —N(CH$_3$)$_2$ | m.p. 112–115° C. |
| 1.197 | 2-(thio)pyridine | H | —CH$_3$ | m.p. 117–119° C. |
| 1.198 | 3-chloro-5-trifluoromethyl-2-(oxy)pyridine | 5-Cl | —CH$_3$ | m.p. 175–179° C. |
| 1.199 | 3-chloro-5-trifluoromethyl-2-(oxy)pyridine | 5-Br | —N(CH$_3$)$_2$ | m.p. 160–162° C. |
| 1.200 | 3-chloro-5-trifluoromethyl-2-(thio)pyridine | H | —N(CH$_3$)$_2$ | m.p. >200° C. |
| 1.201 | 5-ethyl-4-chloro-3-(oxy)pyrimidine | 4-Br | —CH$_3$ | m.p. 202–205° C. |
| 1.202 | 5-propyl-4-chloro-3-(oxy)pyrimidine | H | —N(CH$_3$)$_2$ | m.p. 142–147° C. |

TABLE 1-continued

Compounds of the formula

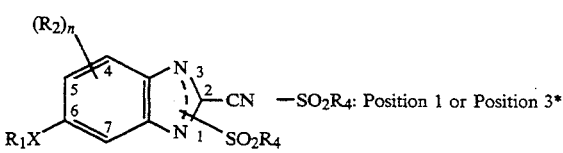  —SO₂R₄: Position 1 or Position 3*

| Comp. No. | R₁X | (R₂)ₙ | R₄ | Physical data |
|---|---|---|---|---|
| 1.203 | CH₃O, Cl, N, O—, N (structure) | 5-Cl | —CH₃ | m.p. 203–205° C. |
| 1.204 | N, N, O—, Cl, propyl (structure) | H | —CH₃ | m.p. 180–182° C. |
| 1.205 | CH₃O, Cl, N, O—, N (structure) | 5-Cl | —N(CH₃)₂ | m.p. 132–134° C. |
| 1.206 | CH₃O, Cl, N, O—, N (structure) | 5-Cl | —N(CH₃)₂ | m.p. 163–165° C. |
| 1.207 | CF₃, N, O— (structure) | 5-Cl | —N(CH₃)₂ | m.p. 130–131° C. |
| 1.208 | CF₃, N, O— (structure) | 5-Cl | —N(CH₃)₂ | m.p. 141–143° C. |
| 1.209 | Cl, CH₃, N, O—, N (structure) | 5-Cl | —N(CH₃)₂ | m.p. 180° C. decomp. |
| 1.210 | N, N, O—, Cl, CH₃ (structure) | 5-Cl | —N(CH₃)₂ | m.p. 204–206° C. |
| 1.211 | N, N, O—, Cl, CH₃ (structure) | 5-Cl | —CH₃ | m.p. 203–205° C. |
| 1.212 | N, N, O—, Cl, CH₃ (structure) | 5-Cl | —CH₃ | m.p. 206–107° C. |

TABLE 1-continued

Compounds of the formula

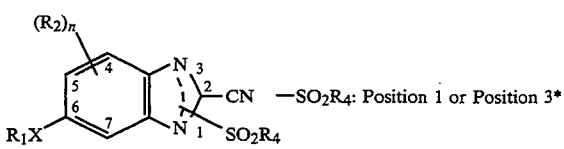

—SO₂R₄: Position 1 or Position 3*

| Comp. No. | R₁X | (R₂)ₙ | R₄ | Physical data |
|---|---|---|---|---|
| 1.213 | Cl, CH₃, N, O—, N (structure) | 5-Cl | —CH₃ | m.p. 210–213° C. |
| 1.214 | Cl, CH₃, N, O—, N (structure) | 5-Cl | —CH₃ | m.p. 221–222° C. |
| 1.215 | iPr, N, O—, Cl, CH₃, N (structure) | 5-Cl | —CH₃ | m.p. 180–182° C. |
| 1.216 | iPr, N, O—, Cl, CH₃, N (structure) | 5-Cl | —N(CH₃)₂ | m.p. 149–152° C. |
| 1.217 | N, O—, CF₃, N (structure) | 5-Cl | —CH₃ | m.p. 207–208° C. |
| 1.218 | N, O—, CF₃, N (structure) | 5-Cl | —N(CH₃)₂ | m.p. 185–186° C. |
| 1.219 | N, O—, Cl, CH₃, N (structure) | H | —CH₃ | m.p. 209–210° C. |
| 1.220 | N, O—, Cl, CH₃, N (structure) | H | —N(CH₃)₂ | m.p. 158–159° C. |
| 1.221 | N, O—, Cl, Et, N (structure) | CF₃ | —CH₃ | m.p. 183–187° C. |

TABLE 1-continued

Compounds of the formula

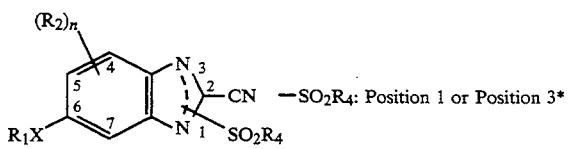

—SO$_2$R$_4$: Position 1 or Position 3*

| Comp. No. | R$_1$X | (R$_2$)$_n$ | R$_4$ | Physical data |
|---|---|---|---|---|
| 1.222 | CH$_3$, N, O—, S (ring) | H | —N(CH$_3$)$_2$ | m.p. 146–160° C. |
| 1.223 | CH$_3$, N, O—, S (ring) | H | —CH$_3$ | m.p. 109–128° C. |
| 1.224 | N, N, O—, Cl, Et (ring) | Cl | —N(CH$_3$)$_2$ | m.p. 157–161° C. |
| 1.225 | N, N, O—, Cl, Et (ring) | Cl | —CH$_3$ | m.p. 199–201° C. |
| 1.226 | N, N, O—, Cl (ring) | CH$_3$ | —CH$_3$ | m.p. 182–186° C. |
| 1.227 | Cl, N, O—, CF$_3$ (ring) | H | —N(CH$_3$)$_2$ | m.p. 145–149° C. |
| 1.228 | Cl, N, O—, CF$_3$ (ring) | H | —CH$_3$ | m.p. 150–153° C. |
| 1.229 | Cl, N, O—, CF$_3$ (ring) | H | —CH$_3$ | m.p. 144–147° C. |
| 1.230 | N, O—, Cl, CF$_3$ (ring) | CH$_3$ | —N(CH$_3$)$_2$ | m.p. 137–143° C. |
| 1.231 | N, N, O—, CF$_3$ (ring) | H | —N(CH$_3$)$_2$ | m.p. 125–130° C. |

TABLE 1-continued

Compounds of the formula

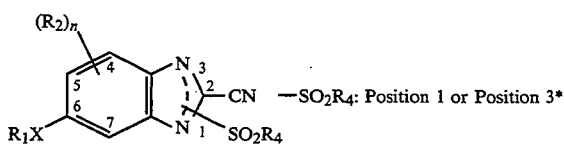

—SO$_2$R$_4$: Position 1 or Position 3*

| Comp. No. | R$_1$X | (R$_2$)$_n$ | R$_4$ | Physical data |
|---|---|---|---|---|
| 1.232 | pyrimidine with O—, CF$_3$ | H | —CH$_3$ | m.p. 126–134° C. |
| 1.233 | pyridine with Cl, O—, CF$_3$ | H | —N(CH$_3$)$_2$ | solid |
| 1.234 | pyridine with Cl, O—, CF$_3$ | H | —N(CH$_3$)$_2$ | solid |
| 1.235 | pyridine with Cl, O—, CF$_3$ | H | —CH$_3$ | m.p. 169–170° C. |
| 1.236 | pyridine with Cl, O—, CF$_3$ | H | —CH$_3$ | m.p. 134–136° C. |
| 1.237 | pyridine with Cl, O—, CF$_3$ | H | —N(CH$_3$)$_2$ | m.p. 184–185° C. |
| 1.238 | pyridine with Cl, O—, CF$_3$ | Cl | —CH$_3$ | m.p. 165–166° C. |
| 1.239 | pyridine with CF$_3$, O— | H | —N(CH$_3$)$_2$ | m.p. 95–96° C. |
| 1.240 | pyridine with Cl, O— | H | —N(CH$_3$)$_2$ | m.p. 155–160° C. |
| 1.241 | pyridine with CH$_3$, O—, CF$_3$ | H | —N(CH$_3$)$_2$ | m.p. 103–105° C. |

TABLE 1-continued

Compounds of the formula

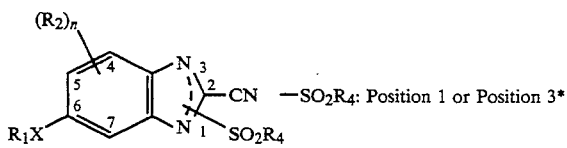

—SO$_2$R$_4$: Position 1 or Position 3*

| Comp. No. | R$_1$X | (R$_2$)$_n$ | R$_4$ | Physical data |
|---|---|---|---|---|
| 1.242 | (pyrimidine with OMe, Cl, Et substituents) | H | —CH$_3$ | m.p. 165–167° C. |
| 1.243 | (pyrimidine with OMe, Cl, Et substituents) | H | —N(CH$_3$)$_2$ | m.p. 98–105° C. |
| 1.244 | CF$_3$-pyridine-O— | H | —N(CH$_3$)$_2$ | m.p. 137–140° C. |
| 1.245 | CF$_3$-pyridine-O— | H | —N(CH$_3$)$_2$ | m.p. 117–118° C. |
| 1.246 | Cl-pyridine-O— | H | —CH$_3$ | m.p. 155–157° C. |
| 1.247 | CH$_3$-pyridine(CF$_3$)-O— | H | —CH$_3$ | m.p. 126–127° C. |
| 1.248 | CF$_3$-pyridine-O— | H | —CH$_3$ | m.p. 124–125° C. |
| 1.249 | pyridine(CF$_3$)-O— | H | —CH$_3$ | m.p. 131–132° C. |
| 1.250 | pyridinone-Cl | H | —N(CH$_3$)$_2$ | m.p. 144–145.5° C. |
| 1.251 | pyridinone-Cl | H | —CH$_3$ | m.p. 138–143° C. |

TABLE 1-continued
Compounds of the formula
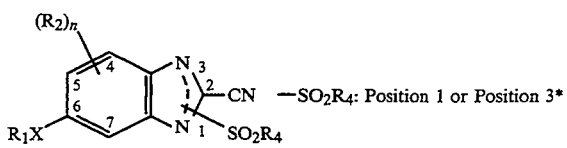
—SO₂R₄: Position 1 or Position 3*
| Comp. No. | R₁X | (R₂)ₙ | R₄ | Physical data |
|---|---|---|---|---|
| 1.252 | CF₃-(N=/S)-O— | H | —N(CH₃)₂ | m.p. 123–125° C. |
| 1.253 | CF₃-(N=/S)-O— | 5-Cl | —N(CH₃)₂ | m.p. 182–186° C. |
| 1.254 | CF₃-(N=/S)-O— | 5-Cl | —CH₃ | m.p. 185–188° C. |
| 1.255 | CF₃-(N=/S)-O— | H | —CH₃ | m.p. 168–169° C. |
| 1.256 | CH₃-(N=/S)-O— | 5-Cl | —CH₃ | |
| 1.257 | CH₃-(N=/S)-O— | 5-Cl | —N(CH₃)₂ | |
| 1.258 | CH₃-(N=/S)-O— | 4-Br | —N(CH₃)₂ | |
| 1.259 | CF₃-(N=/S)-O— | 4-Br | —N(CH₃)₂ | |
| 1.260 | CF₃-(N=/S)-O— | 4-Br | —CH₃ | |
| 1.261 | CF₃-(N=/S)-O— | 5-Br | —N(CH₃)₂ | |
| 1.262 | CF₃-(N=/S)-O— | 5-Br | —CH₃ | |

TABLE 1-continued

Compounds of the formula

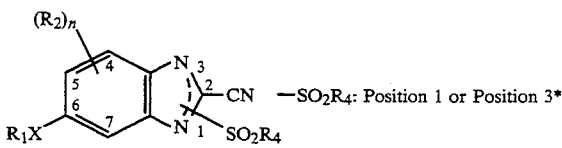
—SO$_2$R$_4$: Position 1 or Position 3*

| Comp. No. | R$_1$X | (R$_2$)$_n$ | R$_4$ | Physical data |
|---|---|---|---|---|
| 1.263 | CH$_3$-[methyl-thiazolyl-O—] | 5-BR | —N(CH$_3$)$_2$ | |
| 1.264 | CH$_3$-[methyl-thiazolyl-O—] | 5-Br | —BH$_3$ | |
| 1.265 | [pyridin-2-yl-S—] | 5-Cl | —N(CH$_3$)$_2$ | m.p. 169–170° C. |
| 1.266 | [pyridin-2-yl-S—] | 5-Cl | —N(CH$_3$)$_2$ | m.p. 142–143° C. |
| 1.267 | [3,5-dichloropyridin-2-yl-S—] | 4-Br | —CH$_3$ | m.p. 230–232° C. |
| 1.268 | [3,5-dichloropyridin-2-yl-S—] | 4-Br | —N(CH$_3$)$_2$ | m.p. 186–187° C. |
| 1.269 | [3,5-dichloropyridin-2-yl-S—] | H | —CH$_3$ | m.p. 157–159° C. |
| 1.270 | [3-CF$_3$-5-Cl-pyridin-2-yl-O—] | 5-Cl | —N(CH$_3$)$_2$ | m.p. 143–145° C. |
| 1.271 | [3-Cl-5-CF$_3$-pyridin-2-yl-S—] | 4-Br | —CH$_3$ | m.p. 201–203° C. |
| 1.272 | [3-Cl-5-CF$_3$-pyridin-2-yl-S—] | 4-Br | —N(CH$_3$)$_2$ | m.p. 203–204° C. |

TABLE 1-continued

Compounds of the formula

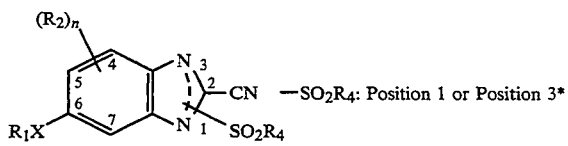
—SO₂R₄: Position 1 or Position 3*

| Comp. No. | R₁X | (R₂)ₙ | R₄ | Physical data |
|---|---|---|---|---|
| 1.273 | ![pyridyl]N⌬S— | 5-Cl | —CH₃ | m.p. 164–167° C. |
| 1.274 | ![pyridyl]N⌬S— | 5-Cl | —N(CH₃)₂ | m.p. 166–168° C. |
| 1.275 | CF₃-pyridyl-S— | 4-Br | —CH₃ | m.p. 197–198° C. |
| 1.276 | CF₃-pyridyl-S— | 4-Br | —N(CH₃)₂ | m.p. 131–133° C. |
| 1.277 | CF₃-pyridyl-S— | H | —CH₃ | m.p. 164–166° C. |
| 1.278 | CF₃-pyridyl-S— | H | —N(CH₃)₂ | m.p. 131–133° C. |
| 1.279 | CF₃-pyridyl-S— | 4-Cl | —CH₃ | m.p. 197–200° C. |
| 1.280 | CF₃-pyridyl-S— | 4-Cl | —N(CH₃)₂ | m.p. 153–154° C. |
| 1.281 | CF₃-pyridyl-S— | 4-Br | —CH₃ | m.p. 155–158° C. |
| 1.282 | CF₃-pyridyl-S— | 4-Br | —N(CH₃)₂ | m.p. 190–192° C. |
| 1.283 | CF₃-pyridyl-S— | H | —CH₃ | m.p. 198–201° C. |

TABLE 1-continued

Compounds of the formula

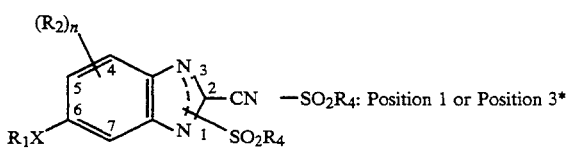

—SO$_2$R$_4$: Position 1 or Position 3*

| Comp. No. | R$_1$X | (R$_2$)$_n$ | R$_4$ | Physical data |
|---|---|---|---|---|
| 1.284 | ![CF$_3$-pyridine-S—] | H | —N(CH$_3$)$_2$ | m.p. 85–88° C. |
| 1.285 | ![OCH$_3$, CH$_3$O-pyrimidine-S—] | H | —N(CH$_3$)$_2$ | m.p. 140–142° C. |
| 1.286 | ![pyrimidine-S—] | 5-Cl | —CH$_3$ | m.p. 146–149° C. |
| 1.287 | ![pyrimidine-S—] | 5-Cl | —N(CH$_3$)$_2$ | m.p. 155–165° C. |
| 1.288 | ![4,6-dimethylpyrimidine-S—] | H | —N(CH$_3$)$_2$ | m.p. 126–130° C. |
| 1.289 | ![4,6-dimethylpyrimidine-S—] | 5-Cl | —N(CH$_3$)$_2$ | m.p. 183–187° C. |
| 1.290 | ![4,6-dimethylpyrimidine-S—] | H | —CH$_3$ | m.p. 152–155° C. |
| 1.291 | ![4-methylpyrimidine-S—] | H | —N(CH$_3$)$_2$ | m.p. 132–142° C. |
| 1.292 | ![5-methylpyrimidine-S—] | H | —CH$_3$ | m.p. 137° C. decomp. |

TABLE 1-continued

Compounds of the formula

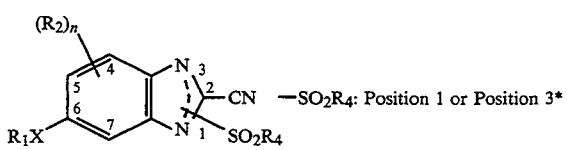
—SO$_2$R$_4$: Position 1 or Position 3*

| Comp. No. | R$_1$X | (R$_2$)$_n$ | R$_4$ | Physical data |
|---|---|---|---|---|
| 1.293 | 4-methyl-5-chloro-6-(thio)pyrimidinyl | 4-Cl | —N(CH$_3$)$_2$ | m.p. 202–204° C. |
| 1.294 | 4-ethyl-5-chloro-6-(thio)pyrimidinyl | H | —N(CH$_3$)$_2$ | m.p. 147–149° C. |
| 1.295 | 4-methyl-5-chloro-6-(thio)pyrimidinyl | 4-Br | —N(CH$_3$)$_2$ | m.p. 201–203° C. |
| 1.296 | 4-methyl-5-chloro-6-(thio)pyrimidinyl | 4-Br | —CH$_3$ | m.p. 216–218° C. |
| 1.297 | 4-methyl-5-chloro-6-(thio)pyrimidinyl | H | —CH$_3$ | m.p. 197–200° C. |
| 1.298 | 4-methyl-5-chloro-6-(thio)pyrimidinyl | H | —N(CH$_3$)$_2$ | m.p. 162–164° C. |
| 1.299 | 3-chloro-2-(thio)pyrazinyl | H | —N(CH$_3$)$_2$ | m.p. 88–90° C. |
| 1.300 | 3-chloro-2-(thio)pyrazinyl | 4-Br | —N(CH$_3$)$_2$ | m.p. 175–177° C. |
| 1.301 | 3-chloro-2-(thio)pyrazinyl | 4-Br | —CH$_3$ | m.p. 178–181° C. |
| 1.302 | 3-methyl-6-(thio)pyridazinyl | H | —CH$_3$ | m.p. 156–160° C. |

TABLE 1-continued

Compounds of the formula

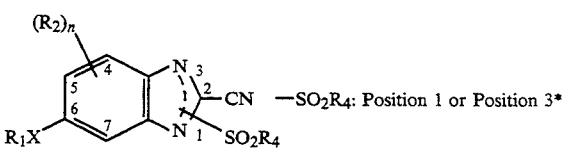

—SO₂R₄: Position 1 or Position 3*

| Comp. No. | R₁X | (R₂)ₙ | R₄ | Physical data |
|---|---|---|---|---|
| 1.303 | CH₃-pyridazine-S- | H | —N(CH₃)₂ | m.p. 125–130° C. |
| 1.304 | Cl-pyridazine-S- | H | —CH₃ | m.p. 194–195° C. |
| 1.305 | Cl-pyridazine-S- | H | —N(CH₃)₂ | m.p. 145–147° C. |
| 1.306 | Cl-pyridazine-S- | 4-Br | —N(CH₃)₂ | m.p. 169–170° C. |
| 1.307 | CF₃-pyridine-O- | 4-Cl | —N(CH₃)₂ | m.p. 158–159° C. |
| 1.308 | Cl,CF₃-pyridine-O- | 4-Cl | —N(CH₃)₂ | m.p. 133–149° C. |
| 1.309 | OCH₃,H₃CO-pyrimidine-O- | H | —CH₃ | |
| 1.310 | OCH₃,H₃CO-pyrimidine-O- | 4-Br | —CH₃ | |
| 1.311 | OCH₃,H₃CO-pyrimidine-O- | H | —N(CH₃)₂ | |
| 1.312 | OCH₃,H₃CO-pyrimidine-O- | 4-Br | —N(CH₃)₂ | |

TABLE 1-continued

Compounds of the formula

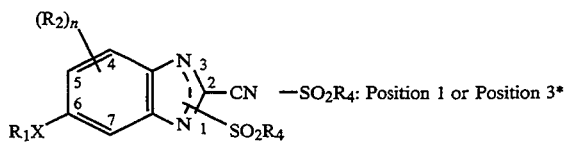

—SO$_2$R$_4$: Position 1 or Position 3*

| Comp. No. | R$_1$X | (R$_2$)$_n$ | R$_4$ | Physical data |
|---|---|---|---|---|
| 1.313 | ![structure: Cl-pyrimidine-O-] | H | —CH$_3$ | |
| 1.314 | ![structure: Cl-pyrimidine-O-] | H | —N(CH$_3$)$_2$ | |
| 1.315 | ![structure: Cl-pyrimidine-O-] | 4-Br | —CH$_3$ | |
| 1.316 | ![structure: Cl-pyrimidine-O-] | 4-Br | —N(CH$_3$)$_2$ | |
| 1.317 | ![structure: C$_2$H$_5$-pyrazine-O-] | H | —CH$_3$ | |
| 1.318 | ![structure: C$_2$H$_5$-pyrazine-O-] | 4-Br | —CH$_3$ | |
| 1.319 | ![structure: C$_2$H$_5$-pyrazine-O-] | H | —N(CH$_3$)$_2$ | |
| 1.320 | ![structure: C$_2$H$_5$-pyrazine-O-] | 4-Br | —N(CH$_3$)$_2$ | |
| 1.321 | ![structure: CH$_3$-pyridazine-O-] | H | —CH$_3$ | |
| 1.322 | ![structure: CH$_3$-pyridazine-O-] | H | —N(CH$_3$)$_2$ | |
| 1.323 | ![structure: CH$_3$-pyridazine-O-] | 4-Br | —CH$_3$ | |

TABLE 1-continued
Compounds of the formula
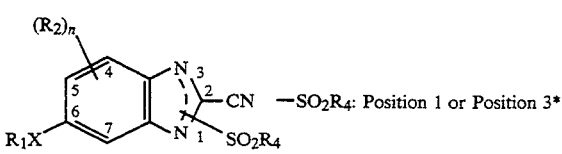
—SO₂R₄: Position 1 or Position 3*
| Comp. No. | R₁X | (R₂)ₙ | R₄ | Physical data |
|---|---|---|---|---|
| 1.324 | CH₃—⟨N=N⟩—O— | 4-Br | —N(CH₃)₂ | |
| 1.325 | H₃O—⟨N=N⟩—O— | H | —CH₃ | |
| 1.326 | H₃O—⟨N=N⟩—O— | 4-Br | —CH₃ | |
| 1.327 | H₃O—⟨N=N⟩—O— | 4-Br | —N(CH₃)₂ | |
| 1.328 | H₃O—⟨N=N⟩—O— | H | —N(CH₃)₂ | |
| 1.329 | Cl—⟨N=N⟩—O— | H | —CH₃ | |
| 1.330 | Cl—⟨N=N⟩—O— | H | —N(CH₃)₂ | |
| 1.331 | Cl—⟨N=N⟩—O— | 4-Br | —CH₃ | |
| 1.332 | Cl—⟨N=N⟩—O— | 4-Br | —N(CH₃)₂ | |
| 1.333 | Cl,Cl—⟨N=N⟩—O— | H | —CH₃ | |
| 1.334 | Cl,Cl—⟨N=N⟩—O— | 4-Br | —N(CH₃)₂ | |

TABLE 1-continued

Compounds of the formula

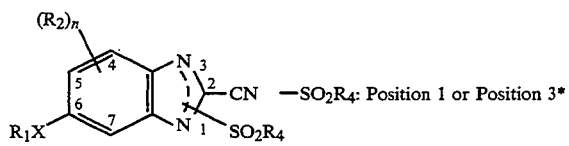

—SO$_2$R$_4$: Position 1 or Position 3*

| Comp. No. | R$_1$X | (R$_2$)$_n$ | R$_4$ | Physical data |
|---|---|---|---|---|
| 1.335 | Cl,Cl-pyridazinyl-O— | H | —N(CH$_3$)$_2$ | |
| 1.336 | Cl,Cl-pyridazinyl-O— | 4-Br | —CH$_3$ | |
| 1.337 | Cl,CF$_3$-pyridyl-S— | 5-Cl | —CH$_3$ | |
| 1.338 | Cl,CF$_3$-pyridyl-S— | 5-Cl | —N(CH$_3$)$_2$ | |
| 1.339 | pyridyl-S— | 4-Br | —CH$_3$ | |
| 1.340 | pyridyl-S— | 4-Br | —N(CH$_3$)$_2$ | m.p. 166–168° C. |
| 1.341 | pyridyl-S— | 5-Br | —CH$_3$ | m.p. 141–142° C. |
| 1.342 | pyridyl-S— | 5-Br | —N(CH$_3$)$_2$ | m.p. 167–169° C. |
| 1.343 | COOEt-pyridyl-O— | H | —N(CH$_3$)$_2$ | m.p. 103–107° C. |
| 1.344 | EtOOC-pyridyl-O— | 4-Br | —N(CH$_3$)$_2$ | m.p. 162–165° C. |

TABLE 1-continued

Compounds of the formula

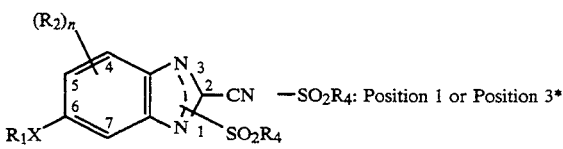  —SO₂R₄: Position 1 or Position 3*

| Comp. No. | R₁X | (R₂)ₙ | R₄ | Physical data |
|---|---|---|---|---|
| 1.345 | cyclopropyl-CH=C(N=)-C(CH₃)=N-O— | 5-Cl | —N(CH₃)₂ | m.p. 164–166° C. |
| 1.346 | cyclopropyl-CH=C(N=)-C(CH₃)=N-O— | 5-Cl | —CH₃ | m.p. 173–175° C. |
| 1.347 | 2,4-(CH₃)₂-6-CN-C₆H₂-S— | 5-Cl | —N(CH₃)₂ | m.p. 186–190° C. |
| 1.348 | 2,4-(CH₃)₂-6-CN-C₆H₂-S— | 5-Cl | —CH₃ | m.p. 199–203° C. |
| 1.349 | 6-CF₃-pyridin-2-yl-O— | 5-Cl | —N(CH₃)₂ | m.p. 166–170° C. |
| 1.350 | 6-CF₃-pyridin-2-yl-O— | 5-Cl | —CH₃ | m.p. 156–160° C. |
| 1.351 | 6-OCH₃-pyrimidin-4-yl-O— | 5-Cl | —N(CH₃)₂ | m.p. 149–152° C. |
| 1.352 | 6-OCH₃-pyrimidin-4-yl-O— | 5-Cl | —CH₃ | m.p. 162–165° C. |
| 1.353 | 5-(CH₃CH₂S)-4,6-(CH₃)₂-pyrimidin-2-yl-O— | 5-Cl | —CH₃ | m.p. 160–165° C. |

TABLE 1-continued

Compounds of the formula $$\text{(structure: benzimidazole with } (R_2)_n \text{ on positions 4-7, } R_1X \text{ at position 6, CN and } SO_2R_4 \text{ substituents)}$$

—SO$_2$R$_4$: Position 1 or Position 3*

| Comp. No. | R$_1$X | (R$_2$)$_n$ | R$_4$ | Physical data |
|---|---|---|---|---|
| 1.354 | CH$_3$CH$_2$S–C(=C(CH$_3$)–N=C(–O–)–N=C(CH$_3$))–CH$_3$ (pyrimidine) | 5-Cl | —N(CH$_3$)$_2$ | m.p. 112–115° C. |
| 1.355 | Cl–C(=C(CH$_3$)–N=C(–O–)–N=C(CH$_3$)) (pyrimidine) | 5-Cl | —N(CH$_3$)$_2$ | m.p. 183–185° C. |
| 1.356 | CH$_3$–C(=N–)–N=C(–O–)–C(Cl)=C(CH$_3$) (pyrimidine) | 5-Cl | —N(CH$_3$)$_2$ | m.p. 190–193° C. |
| 1.357 | CF$_3$, CH$_3$CH$_2$OOC– substituted thiazole with –O– | 5-Cl | —N(CH$_3$)$_2$ | m.p. 136–139° C. |
| 1.358 | CF$_3$, Cl substituted pyridine with –O– | 7-Cl | —N(CH$_3$)$_2$ | m.p. 186–188° C. |
| 1.359 | pyrimidine with Cl, CH$_3$, –O– | 4-Br | —N(CH$_3$)$_2$ | m.p. 214–250° C. |
| 1.360 | pyrimidine with CH$_3$, Cl, –O– | 4-Br | —CH$_3$ | m.p. 179–184° C. |
| 1.361 | pyrimidine with Cl, ethyl, –O– | 4-Br | —N(CH$_3$)$_2$ | m.p. 205–209° C. |

*Isomer mixture AB with regard to —SO$_2$R$_4$ in position 1 or 3: or the pure isomers A or B.

TABLE 2
Compounds of the formula
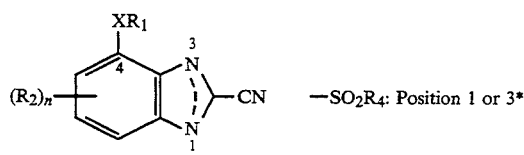   —SO$_2$R$_4$: Position 1 or 3*
| Comp. No. | R$_1$X | (R$_2$)$_n$ | R$_4$ | Physical data |
|---|---|---|---|---|
| 2.1 | 2-pyridyl-O— | H | —CH$_3$ | |
| 2.2 | 2-pyridyl-O— | 5-Cl | —CH$_3$ | |
| 2.3 | 2-pyridyl-O— | H | —N(CH$_3$)$_2$ | |
| 2.4 | 5-CF$_3$-2-pyridyl-O— | H | —CH$_3$ | |
| 2.5 | 5-Br-2-pyridyl-O— | H | —CH$_3$ | |
| 2.6 | thiazol-2-yl-O— | H | —CH$_3$ | |
| 2.7 | 3,5-diCl-2-pyridyl-O— | H | —CH$_3$ | |
| 2.8 | 2-pyridyl-O— | 6-F | —CH$_3$ | |
| 2.9 | 5-CF$_3$-2-pyridyl-O— | 6-F | —CH$_3$ | |
| 2.10 | thiazol-2-yl-O— | 6-F | —CH$_3$ | |
| 2.11 | 5-Br-2-pyridyl-O— | 6-F | —CH$_3$ | |

TABLE 2-continued
Compounds of the formula
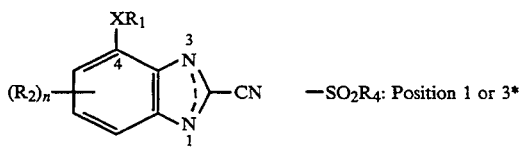
—SO$_2$R$_4$: Position 1 or 3*
| Comp. No. | R$_1$X | (R$_2$)$_n$ | R$_4$ | Physical data |
|---|---|---|---|---|
| 2.12 | 5-Cl, 3-F, 2-O— pyridine | H | —CH$_3$ | |
| 2.13 | 5-F$_3$C, 2-O— pyridine | 6-F | —N(CH$_3$)$_2$ | |
| 2.14 | thiazol-2-yl-O— | 6-Cl | —CH$_3$ | |
| 2.15 | pyridin-2-yl-O— | 6-F | —N(CH$_3$)$_2$ | |
| 2.16 | 5-F$_3$C, 2-O— pyridine | 5-Cl | —CH$_3$ | |
| 2.17 | thiazol-2-yl-O— | 6-CF$_3$ | —CH$_3$ | |
| 2.18 | pyridin-2-yl-O— | 6-Cl | —CH$_3$ | |
| 2.19 | 5-Br, 2-O— pyridine | 6-F | —N(CH$_3$)$_2$ | |
| 2.20 | 5-Br, 2-O— pyridine | 6-Cl | —CH$_3$ | |
| 2.21 | pyridin-2-yl-O— | 6-Cl | —N(CH$_3$)$_2$ | |
| 2.22 | 5-F$_3$C, 2-O— pyridine | 6-Cl | —CH$_3$ | |

TABLE 2-continued

Compounds of the formula

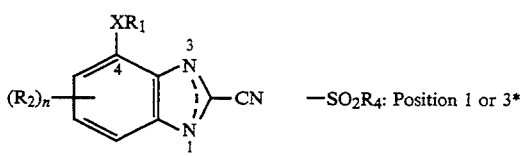

—SO$_2$R$_4$: Position 1 or 3*

| Comp. No. | R$_1$X | (R$_2$)$_n$ | R$_4$ | Physical data |
|---|---|---|---|---|
| 2.23 | 3,5-dichloro-2-pyridyloxy | 6-F | —CH$_3$ | |
| 2.24 | 5-chloro-3-fluoro-2-pyridyloxy | 5-F | —CH$_3$ | |
| 2.25 | 3-chloro-5-trifluoromethyl-2-pyridyloxy | H | —CH$_3$ | |
| 2.26 | 3-chloro-5-trifluoromethyl-2-pyridyloxy | 6-CF$_3$ | —CH$_3$ | |
| 2.27 | 2-thienyloxy | H | —CH$_3$ | |
| 2.28 | 5-bromo-2-pyridyloxy | 6-CF$_3$ | —CH$_3$ | |
| 2.29 | 5-trifluoromethyl-2-pyridyloxy | 6-Cl | —N(CH$_3$)$_2$ | |
| 2.30 | 3,5-dichloro-2-pyridyloxy | 6-F | —N(CH$_3$)$_2$ | |
| 2.31 | 2-thienyloxy | 6-F | —CH$_3$ | |
| 2.32 | 5-chloro-3-fluoro-2-pyridyloxy | 6-F | —CH$_3$ | |
| 2.33 | 3-chloro-5-trifluoromethyl-2-pyridyloxy | 5-F | —CH$_3$ | |
| 2.34 | 2-thienyloxy | 6-Cl | —CH$_3$ | |

TABLE 2-continued

Compounds of the formula

[Structure: benzimidazole-2-carbonitrile with XR₁ at position 4, (R₂)ₙ on benzene ring, N at positions 1 and 3]  —SO₂R₄: Position 1 or 3*

| Comp. No. | R₁X | (R₂)ₙ | R₄ | Physical data |
|---|---|---|---|---|
| 2.35 | 2-pyridyl-O— | 6-CF₃ | —CH₃ | |
| 2.36 | 5-bromo-2-pyridyl-O— | 6-CF₃ | —N(CH₃)₂ | |
| 2.37 | 5-trifluoromethyl-2-pyridyl-O— | 6-CF₃ | —CH₃ | |
| 2.38 | 2-thienyl-O— | 6-CF₃ | —CH₃ | |
| 2.39 | 5-bromo-2-pyridyl-O— | 6-CH₃ | —CH₃ | |
| 2.40 | 3,5-dichloro-2-pyridyl-O— | 6-Cl | —CH₃ | |
| 2.41 | 3,5-dichloro-2-pyridyl-O— | 6-Cl | cyclohexyl | |
| 2.42 | 5-chloro-3-fluoro-2-pyridyl-O— | 6-F | —N(CH₃)₂ | |
| 2.43 | 5-trifluoromethyl-2-pyridyl-O— | 6-CH₃ | —CH₃ | |
| 2.44 | 2-pyridyl-O— | 5-Cl, 7-F | —CH₃ | |
| 2.45 | 5-chloro-2-pyridyl-O— | H | —CH₃ | |

TABLE 2-continued

Compounds of the formula

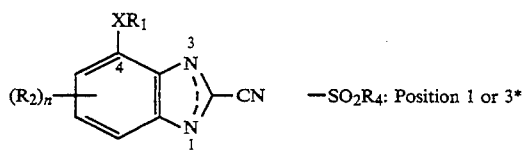
—SO$_2$R$_4$: Position 1 or 3*

| Comp. No. | R$_1$X | (R$_2$)$_n$ | R$_4$ | Physical data |
|---|---|---|---|---|
| 2.46 | 3,5-dichloropyridin-2-yloxy | 6-CF$_3$ | —CH$_3$ | |
| 2.47 | 3-chloro-5-trifluoromethylpyridin-2-yloxy | 6-F | —CH$_3$ | |
| 2.48 | 5-chloropyridin-2-yloxy | 5-F | —CH$_3$ | |
| 2.49 | 5-chloro-3-fluoropyridin-2-yloxy | 6-Cl | —CH$_3$ | |
| 2.50 | 3-chloro-5-trifluoromethylpyridin-2-yloxy | 6-F | —N(CH$_3$)$_2$ | |
| 2.51 | 5-chloropyridin-2-yloxy | 6-F | —CH$_3$ | |
| 2.52 | 3,5-dichloropyridin-2-yloxy | 6-CF$_3$ | —N(CH$_3$)$_2$ | |
| 2.53 | 3-chloro-5-trifluoromethylpyridin-2-yloxy | 5-Cl | —CH$_3$ | |
| 2.54 | 3-chloro-5-trifluoromethylpyridin-2-yloxy | 6-CH$_3$ | —CH$_3$ | |
| 2.55 | 5-chloro-3-fluoropyridin-2-yloxy | 6-Cl | —N(CH$_3$)$_2$ | |
| 2.56 | 5-chloropyridin-2-yloxy | 6-F | —N(CH$_3$)$_2$ | |

TABLE 2-continued

Compounds of the formula

XR₁ at position 3, (R₂)ₙ on benzene ring at position 4, benzimidazole with −CN at 2-position, −SO₂R₄: Position 1 or 3*

| Comp. No. | R₁X | (R₂)ₙ | R₄ | Physical data |
|---|---|---|---|---|
| 2.57 | 5-Cl, 3-F-pyridin-2-yloxy | 6-CF₃ | −CH₃ | |
| 2.58 | 5-Cl-pyridin-2-yloxy | 6-CH₃ | −CH₃ | |
| 2.59 | 5-CF₃, 3-Cl-pyridin-2-yloxy | 6-Cl | −CH₃ | |
| 2.60 | 5-CF₃, 3-Cl-pyridin-2-yloxy | 5-Cl, 6-Cl | −CH₃ | |
| 2.61 | 5-Cl, 3-Cl-pyridin-2-yloxy | 6-CH₃ | −CH₃ | |
| 2.62 | 5-Cl, 3-F-pyridin-2-yloxy | 6-CF₃ | −N(CH₃)(C₂H₅) | |
| 2.63 | 5-Cl-pyridin-2-yloxy | 6-Cl | −CH₃ | |
| 2.64 | 5-CF₃, 3-Cl-pyridin-2-yloxy | 6-Cl | −N(CH₃)₂ | |
| 2.65 | 6-CH₃-pyridin-2-yloxy | H | −CH₃ | |
| 2.66 | 5-CF₃, 3-Cl-pyridin-2-yloxy | 7-Cl | −CH₃ | |
| 2.67 | 5-Cl, 3-F-pyridin-2-yloxy | 6-CF₃ | −N(CH₃)₂ | |

TABLE 2-continued

Compounds of the formula

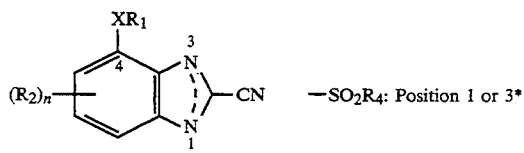

—SO$_2$R$_4$: Position 1 or 3*

| Comp. No. | R$_1$X | (R$_2$)$_n$ | R$_4$ | Physical data |
|---|---|---|---|---|
| 2.68 | 6-methylpyridin-2-yloxy (CH$_3$-pyridine-O—) | 6-F | —CH$_3$ | |
| 2.69 | 3-chloro-5-trifluoromethylpyridin-2-yloxy | 5-CF$_3$ | —CH$_3$ | |
| 2.70 | 3,5-dichloropyridin-2-yloxy | 6-Cl | —N(CH$_3$)$_2$ | |
| 2.71 | 5-chloro-3-fluoropyridin-2-yloxy | 6-CH$_3$ | —CH$_3$ | |
| 2.72 | 3-chloro-5-trifluoromethylpyridin-2-yloxy | 6-CF$_3$ | —CH$_3$ | |
| 2.73 | 6-methylpyridin-2-yloxy | 6-Cl | —CH$_3$ | |
| 2.74 | 5-chloropyridin-2-yloxy | 6-CF$_3$ | —CH$_3$ | |
| 2.75 | 6-methylpyridin-2-yloxy | 6-CF$_3$ | —CH$_3$ | |
| 2.76 | 5-chloropyridin-2-ylthio | H | —CH$_3$ | |
| 2.77 | 3,5-dichloropyridin-2-ylthio | 5-Cl | —N(CH$_3$)$_2$ | |
| 2.78 | 3-chloropyridin-2-ylthio | H | —N(CH$_3$)$_2$ | |

TABLE 2-continued

Compounds of the formula

[Structure: benzimidazole with XR₁ at position 4, (R₂)ₙ substituent, CN at position 2, and N atoms at positions 1 and 3]   —SO₂R₄: Position 1 or 3*

| Comp. No. | R₁X | (R₂)ₙ | R₄ | Physical data |
|---|---|---|---|---|
| 2.79 | 3-Cl, 5-CF₃-pyridin-2-yl-S— | 5-Br | —CH₃ | |
| 2.80 | 5-CF₃-pyridin-2-yl-S— | H | —N(CH₃)₂ | |
| 2.81 | 3-Cl, 5-CF₃-pyridin-2-yl-S— | H | —CH₃ | |
| 2.82 | 2,4-dimethoxy-pyrimidin-6-yl-S— | H | —N(CH₃)₂ | |
| 2.83 | 4,6-dimethyl-pyrimidin-2-yl-S— | 6-CF₃ | —CH₃ | |
| 2.84 | 2-methoxy-pyrimidin-4-yl-S— | 6-F | —N(CH₃)₂ | |
| 2.85 | pyrazin-2-yl-S— | H | —CH₃ | |
| 2.86 | 3-chloro-pyrazin-2-yl-S— | 5-Cl | —N(CH₃)₂ | |
| 2.87 | 3,6-dimethyl-pyrazin-2-yl-S— | 6-Cl | —CH₃ | |

*Isomer mixtures AB with regard to —SO₂R₄ in position 1 or 3, or the pure isomers A or B.

TABLE 3

Compounds of the formula

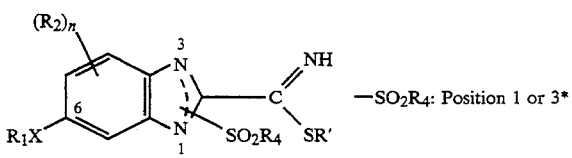

—SO₂R₄: Position 1 or 3*

(if R' = H, then the compound is in the tautomeric form —C(S)—NH₂)

| Comp. No. | R₁X | (R₂)ₙ | R₄ | R' | Physical data |
|---|---|---|---|---|---|
| 3.1 | 2-pyridyl-O— | H | —CH₃ | H | |
| 3.2 | 3,5-dichloro-2-pyridyl-O— | H | —CH₃ | H | |
| 3.3 | 3-chloro-5-trifluoromethyl-2-pyridyl-O— | 5-Cl | —CH₃ | H | |
| 3.4 | 2-pyridyl-O— | H | —CH₃ | —CH₃ | |
| 3.5 | 2-pyridyl-O— | H | —N(CH₃)₂ | H | |
| 3.6 | 3,5-dichloro-2-pyridyl-O— | H | —N(CH₃)₂ | H | |
| 3.7 | 3-chloro-5-trifluoromethyl-2-pyridyl-O— | 5-Cl | —N(CH₃)₂ | H | |
| 3.8 | 2-pyridyl-O— | H | —N(CH₃)₂ | —CH₃ | |
| 3.9 | 3,5-dichloro-2-pyridyl-O— | H | —N(CH₃)₂ | benzyl | |
| 3.10 | 3-chloro-5-trifluoromethyl-2-pyridyl-O— | 5-F | CH₃ | H | |
| 3.11 | 3-chloro-5-trifluoromethyl-2-pyridyl-O— | 5-Cl | —N(CH₃)₂ | —CH₃ | |

TABLE 3-continued
Compounds of the formula
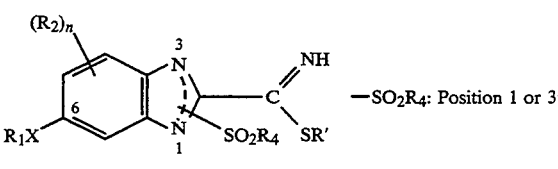
—SO$_2$R$_4$: Position 1 or 3*
(if R' = H, then the compound is in the tautomeric form —C(S)—NH$_2$)
| Comp. No. | R$_1$X | (R$_2$)$_n$ | R$_4$ | R' | Physical data |
|---|---|---|---|---|---|
| 3.12 | 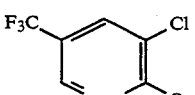 | 5-Br | —N(CH$_3$)$_2$ | H | |
| 3.13 |  | 5-F | —CH$_3$ | benzyl | |
| 3.14 | 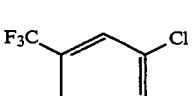 | 4-F | —N(CH$_3$)$_2$ | H | |
| 3.15 | 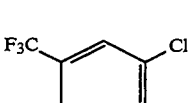 | 5-Br | —N(CH$_3$)$_2$ | —CH$_3$ | |
| 3.16 | 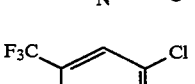 | 5-F | —N(CH$_3$)$_2$ | H | |
| 3.17 | 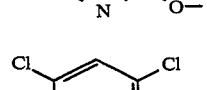 | 5-CH$_3$ | —CH$_3$ | H | |
| 3.18 | 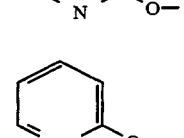 | 4-F | —N(CH$_3$)$_2$ | —CH$_3$ | |
| 3.19 | 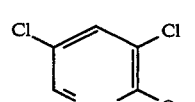 | 5-Cl | —CH$_3$ | H | |
| 3.20 | 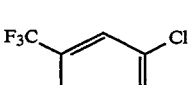 | 5-Cl | —N(CH$_3$)$_2$ | H | |
| 3.21 | 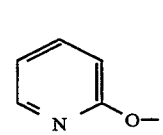 | 5-CH$_3$ | —N(CH$_3$)$_2$ | H | |
| 3.22 |  | 5-Cl | —N(CH$_3$)$_2$ | H | |

TABLE 3-continued

Compounds of the formula

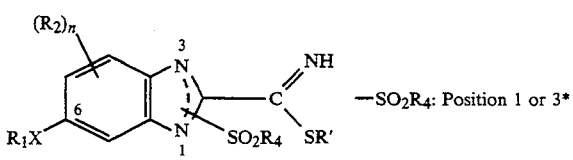

—SO₂R₄: Position 1 or 3*

(if R' = H, then the compound is in the tautomeric form —C(S)—NH₂)

| Comp. No. | R₁X | (R₂)ₙ | R₄ | R' | Physical data |
|---|---|---|---|---|---|
| 3.23 | 3-Cl, 5-CF₃ pyridin-2-yl-O— | 5-CH₃ | —N(CH₃)₂ | —CH₃ | |
| 3.24 | 3,5-diCl pyridin-2-yl-O— | 5-Cl | —N(CH₃)₂ | —C₂H₅ | |
| 3.25 | pyridin-2-yl-O— | 5-Cl | —N(CH₃)₂ | —CH₃ | |
| 3.26 | pyridin-2-yl-O— | 5-CF₃ | —CH₃ | H | |
| 3.27 | 5-CF₃ pyridin-2-yl-O— | H | —CH₃ | H | |
| 3.28 | 3,5-diCl pyridin-2-yl-O— | 5-Br | —N(CH₃)₂ | H | |
| 3.29 | pyridin-2-yl-O— | 5-CF₃ | —N(CH₃)₂ | H | |
| 3.30 | 5-CF₃ pyridin-2-yl-O— | H | —N(CH₃)₂ | H | |
| 3.31 | 3,5-diCl pyridin-2-yl-O— | 5-Br | —N(CH₃)₂ | —CH₃ | |
| 3.32 | 5-CF₃ pyridin-2-yl-O— | H | —N(CH₃)₂ | —CH₃ | |
| 3.33 | 5-CF₃ pyridin-2-yl-O— | 5-F | —CH₃ | H | |

TABLE 3-continued

Compounds of the formula

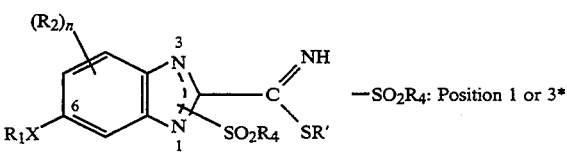

—SO$_2$R$_4$: Position 1 or 3*

(if R' = H, then the compound is in the tautomeric form —C(S)—NH$_2$)

| Comp. No. | R$_1$X | (R$_2$)$_n$ | R$_4$ | R' | Physical data |
|---|---|---|---|---|---|
| 3.34 | F$_3$C–[pyridine–Cl]–O— | H | —CH$_3$ | H | m.p. 181–182° C. |
| 3.35 | F$_3$C–[pyridine]–O— | 5-CF$_3$ | —N(CH$_3$)$_2$ | H | |
| 3.36 | F$_3$C–[pyridine–Cl]–O— | H | —CH$_3$ | —CH$_3$ | |
| 3.37 | F$_3$C–[pyridine]–O— | 5-F | —CH$_3$ | —CH$_3$ | |
| 3.38 | F$_3$C–[pyridine–Cl]–O— | H | —N(CH$_3$)$_2$ | H | |
| 3.39 | F$_3$C–[pyridine–Cl]–O— | 5-OCH$_3$ | —CH$_3$ | H | |
| 3.40 | F$_3$C–[pyridine]–O— | 5-F | —N(CH$_3$)$_2$ | H | |
| 3.41 | F$_3$C–[pyridine]–O— | 5-Br | —N(CH$_3$)$_2$ | H | |
| 3.42 | F$_3$C–[pyridine–Cl]–O— | H | —N(CH$_3$)$_2$ | —CH$_3$ | |
| 3.43 | F$_3$C–[pyridine]–O— | 5-F | —N(CH$_3$)$_2$ | —CH$_3$ | |
| 3.44 | F$_3$C–[pyridine–Cl]–O— | 5-OCH$_3$ | —N(CH$_3$)$_2$ | H | |

TABLE 3-continued

Compounds of the formula

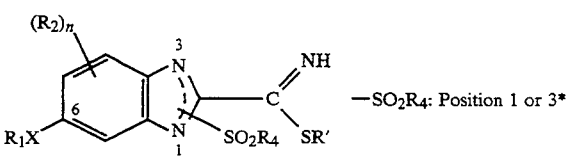

—SO$_2$R$_4$: Position 1 or 3*

(if R' = H, then the compound is in the tautomeric form —C(S)—NH$_2$)

| Comp. No. | R$_1$X | (R$_2$)$_n$ | R$_4$ | R' | Physical data |
|---|---|---|---|---|---|
| 3.45 | F$_3$C—⟨pyridine⟩—O— | 5-Cl | —N(CH$_3$)$_2$ | H | |
| 3.46 | F$_3$C—⟨pyridine, Cl⟩—O— | 5-OCH$_3$ | —N(CH$_3$)$_2$ | H | |
| 3.47 | F$_3$C—⟨pyridine, Cl⟩—O— | 4-F | —N(CH$_3$)$_2$ | H | |
| 3.48 | F$_3$C—⟨pyridine, Cl⟩—O— | 5-F | —CH$_3$ | —C$_2$H$_5$ | |
| 3.49 | F$_3$C—⟨pyridine, Cl⟩—O— | 5-CF$_3$ | —CH$_3$ | H | |
| 3.50 | F$_3$C—⟨pyridine, Cl⟩—O— | 5-CF$_3$ | —N(CH$_3$)$_2$ | H | m.p. 190–192° C. |
| 3.51 | F$_3$C—⟨pyridine, Cl⟩—O— | 5-F | —N(CH$_3$)$_2$ | —CH$_3$ | |
| 3.52 | F$_3$C—⟨pyridine, Cl⟩—O— | 5-CF$_3$ | —N(CH$_3$)$_2$ | —C$_2$H$_5$ | |
| 3.53 | F$_3$C—⟨pyridine, Cl⟩—O— | 5-CF$_3$ | —N(CH$_3$)$_2$ | —CH$_3$ | |
| 3.54 | F$_3$C—⟨pyridine⟩—O— | 5-Cl | —N(CH$_3$)$_2$ | —CH$_3$ | |
| 3.55 | F$_3$C—⟨pyridine, Cl⟩—O— | 5-CF$_3$ | —N(CH$_3$)$_2$ | benzyl | |

TABLE 3-continued

Compounds of the formula

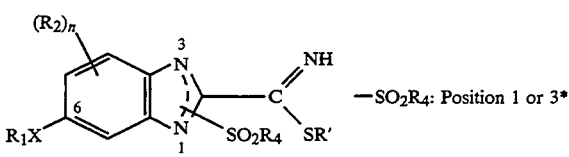

—SO₂R₄: Position 1 or 3*

(if R' = H, then the compound is in the tautomeric form —C(S)—NH₂)

| Comp. No. | R₁X | (R₂)ₙ | R₄ | R' | Physical data |
|---|---|---|---|---|---|
| 3.56 | 2-pyridyl-O— | 5-F | —CH₃ | H | |
| 3.57 | 5-CF₃, 3-Cl-pyridyl-2-O— | 5-F | —N(CH₃)₂ | benzyl | |
| 3.58 | 2-pyridyl-O— | 5-F | —N(CH₃)₂ | H | |
| 3.59 | 5-CF₃-pyridyl-2-O— | 5-CF₃ | —N(CH₃)₂ | —CH₃ | |
| 3.60 | 2-pyridyl-O— | 5-F | —N(CH₃)₂ | —CH₃ | |
| 3.61 | 3-Cl-pyridyl-2-S— | H | —CH₃ | H | |
| 3.62 | 6-CH₃O-pyridyl-2-S— | 4-Br | —CH₃ | H | |
| 3.63 | 5-CF₃, 3-Cl-pyridyl-2-S— | H | —CH₃ | H | |
| 3.64 | 5-CF₃, 3-Cl-pyridyl-2-S— | H | —N(CH₃)₂ | H | |
| 3.65 | 5-CF₃, 3-Cl-pyridyl-2-S— | 5-Cl | —CH₃ | —CH₃ | |
| 3.66 | 5-CF₃, 3-Cl-pyridyl-2-S— | 5-Cl | —N(CH₃)₂ | H | |

TABLE 3-continued

Compounds of the formula (R2)n on benzimidazole (positions 3,6,7,1 shown), with C(=NH)(SR') substituent and —SO2R4: Position 1 or 3*

(if R' = H, then the compound is in the tautomeric form —C(S)—NH2)

| Comp. No. | R1X | (R2)n | R4 | R' | Physical data |
|---|---|---|---|---|---|
| 3.67 | 3-Cl-5-CF3-pyridin-2-yl-S— | 5-Br | —CH3 | H | |
| 3.68 | 3-Cl-5-CF3-pyridin-2-yl-S— | 5-Br | —N(CH3)2 | H | |
| 3.69 | 5-CF3-pyridin-2-yl-S— | 5-OCH3 | —CH3 | H | |
| 3.70 | 3,5-diCl-pyridin-2-yl-S— | H | —CH3 | —CH3 | |
| 3.71 | 4,6-di(OCH3)-pyrimidin-2-yl-S— [with OCH3 and CH3O groups] | 4-Br | —CH3 | H | |
| 3.72 | 4,6-diCH3-pyrimidin-2-yl-S— | 5-Cl | —N(CH3)2 | H | |
| 3.73 | 4,6-di(OCH3)-pyrimidin-2-yl-S— | H | —CH3 | H | |
| 3.74 | pyrazin-2-yl-S— | 4-OCF3 | —CH3 | —CH3 | |
| 3.75 | 3-Cl-pyrazin-2-yl-S— | 5-Cl | —N(CH3)2 | —CH3 | |
| 3.76 | 3,6-diCH3-pyrazin-2-yl-S— | 5-Br | —CH3 | H | |

TABLE 3-continued

Compounds of the formula

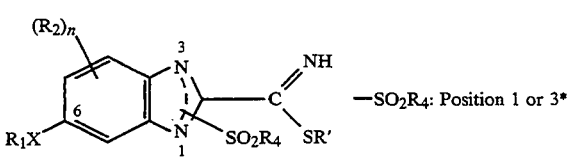

—SO$_2$R$_4$: Position 1 or 3*

(if R' = H, then the compound is in the tautomeric form —C(S)—NH$_2$)

| Comp. No. | R$_1$X | (R$_2$)$_n$ | R$_4$ | R' | Physical data |
|---|---|---|---|---|---|
| 3.77 | [Cl-pyrimidinyl-S—] | 4-CF$_3$ | —N(CH$_3$)$_2$ | H | |
| 3.78 | [pyrimidinyl with Cl, ethyl, O—] | 5-Cl | —N(CH$_3$)$_2$ | H | m.p. 206–208° C. |
| 3.79 | [pyrimidinyl with CF$_3$, O—] | 5-Cl | —N(CH$_3$)$_2$ | H | m.p. 200–203° C. |
| 3.80 | [pyridinyl with Cl, Cl, O—] | 4-Br | —N(CH$_3$)$_2$ | H | m.p. 225–227° C. |
| 3.81 | [CF$_3$-pyridinyl-S—] | 5-Cl | —N(CH$_3$)$_2$ | H | m.p. 147–148° C. |
| 3.82 | [pyridinyl-S—] | 5-Cl | —N(CH$_3$)$_2$ | H | |
| 3.83 | [pyrimidinyl with CH$_3$, Cl, O—] | 5-Cl | —N(CH$_3$)$_2$ | H | m.p. 167–171,5° C. |
| 3.84 | [—O-pyrimidinyl with Cl, CH$_3$] | 5-Cl | —N(CH$_3$)$_2$ | H | amorph |
| 3.85 | [pyrimidinyl with ethyl, Cl, O—] | H | —CH$_3$ | H | m.p. 172–173° C. |

*Isomer mixtures AB with regard to —SO$_2$R$_4$ in position 1 or 3, or the pure isomers A or B.

TABLE 4

Compounds of the formula

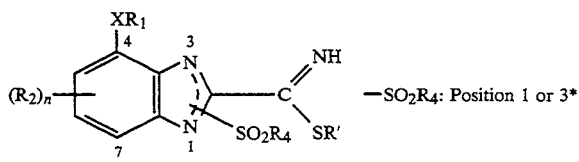
—SO$_2$R$_4$: Position 1 or 3*

| Comp. No. | R$_1$X | (R$_2$)$_n$ | R$_4$ | R' | Physical data |
|---|---|---|---|---|---|
| 4.1 | 2-pyridyl-O— | H | —CH$_3$ | H | |
| 4.2 | 5-CF$_3$-2-pyridyl-O— | 6-Cl | —CH$_3$ | H | |
| 4.3 | 5-CF$_3$-3-Cl-2-pyridyl-O— | H | —CH$_3$ | H | |
| 4.4 | 2-pyridyl-O— | H | —CH$_3$ | —CH$_3$ | |
| 4.5 | 5-Cl-3-F-2-pyridyl-O— | 6-Cl | —CH$_3$ | —CH$_3$ | |
| 4.6 | 2-pyridyl-O— | H | —N(CH$_3$)$_2$ | H | |
| 4.7 | 5-CF$_3$-2-pyridyl-O— | 6-Cl | —CH$_3$ | —CH$_3$ | |
| 4.8 | 5-CF$_3$-3-Cl-2-pyridyl-O— | H | —CH$_3$ | —CH$_3$ | |
| 4.9 | 5-CF$_3$-3-Cl-2-pyridyl-O— | H | —N(CH$_3$)$_2$ | H | |
| 4.10 | 5-CF$_3$-3-Cl-2-pyridyl-O— | 6-CF$_3$ | —N(CH$_3$)$_2$ | —CH$_3$ | |
| 4.11 | 2-pyridyl-O— | H | —N(CH$_3$)$_2$ | —CH$_3$ | |

TABLE 4-continued

Compounds of the formula

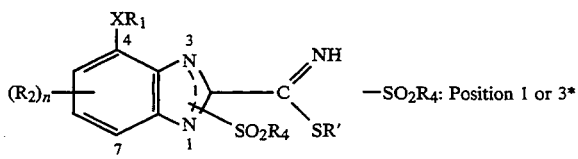
—SO$_2$R$_4$: Position 1 or 3*

| Comp. No. | R$_1$X | (R$_2$)$_n$ | R$_4$ | R' | Physical data |
|---|---|---|---|---|---|
| 4.12 | 2-pyridyl-O— | 6-Cl | —CH$_3$ | —CH$_3$ | |
| 4.13 | 5-CF$_3$-2-pyridyl-O— | 6-Cl | —N(CH$_3$)$_2$ | H | |
| 4.14 | 5-Cl-3-F-2-pyridyl-O— | 6-Cl | —N(CH$_3$)$_2$ | H | |
| 4.15 | 5-CF$_3$-3-Cl-2-pyridyl-O— | H | —N(CH$_3$)$_2$ | —CH$_3$ | |
| 4.16 | 5-CF$_3$-3-Cl-2-pyridyl-O— | 6-CF$_3$ | —N(CH$_3$)$_2$ | —C$_2$H$_5$ | |
| 4.17 | 5-CF$_3$-2-pyridyl-O— | 6-Cl | —N(CH$_3$)$_2$ | —CH$_3$ | |
| 4.18 | 5-Cl-3-F-2-pyridyl-O— | 6-Cl | —N(CH$_3$)$_2$ | —CH$_3$ | |
| 4.19 | 2-pyridyl-O— | 6-Cl | —N(CH$_3$)$_2$ | H | |
| 4.20 | 5-Cl-3-F-2-pyridyl-O— | 6-CH$_3$ | —CH$_3$ | H | |
| 4.21 | 5-Cl-3-CF$_3$-2-pyridyl-O— | H | —N(CH$_3$)$_2$ | —CH$_3$ | |
| 4.22 | 2-pyridyl-O— | 6-Cl | —N(CH$_3$)$_2$ | —CH$_3$ | |

TABLE 4-continued

Compounds of the formula

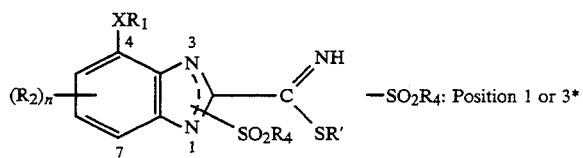

—SO$_2$R$_4$: Position 1 or 3*

| Comp. No. | R$_1$X | (R$_2$)$_n$ | R$_4$ | R' | Physical data |
|---|---|---|---|---|---|
| 4.23 | F$_3$C-pyridyl-O— | 6-Cl | —N(CH$_3$)$_2$ | —C$_2$H$_5$ | |
| 4.24 | Cl,F-pyridyl-O— | 6-CH$_3$ | —CH$_3$ | —CH$_3$ | |
| 4.25 | F$_3$C,Cl-pyridyl-O— | 6-CH$_3$ | —N(CH$_3$)$_2$ | H | |
| 4.26 | pyridyl-O— | 6-CF$_3$ | —N(CH$_3$)$_2$ | H | |
| 4.27 | Cl,F-pyridyl-O— | H | —CH$_3$ | —CH$_3$ | |
| 4.28 | F$_3$C,Cl-pyridyl-O— | 5-F | —N(CH$_3$)$_2$ | H | |
| 4.29 | Cl,F-pyridyl-O— | 6-CH$_3$ | —N(CH$_3$)$_2$ | H | |
| 4.30 | pyridyl-O— | 6-CF$_3$ | —N(CH$_3$)$_2$ | —C$_3$H$_7$-n | |
| 4.31 | F$_3$C-pyridyl-O— | 5-F | —N(CH$_3$)$_2$ | —CH$_3$ | |
| 4.32 | Cl,F-pyridyl-O— | 6-CH$_3$ | —N(CH$_3$)$_2$ | —CH$_3$ | |
| 4.33 | F$_3$C-pyridyl-O— | H | —CH$_3$ | H | |

TABLE 4-continued

Compounds of the formula

[Structure: benzimidazole with XR₁ at position 4, (R₂)ₙ substituent, C(=NH)SR' at position 2, SO₂R₄ at N1; note: —SO₂R₄: Position 1 or 3*]

| Comp. No. | R₁X | (R₂)ₙ | R₄ | R' | Physical data |
|---|---|---|---|---|---|
| 4.34 | 5-Cl, 3-F, 2-O— pyridine | 6-CF₃ | —CH₃ | —CH₃ | |
| 4.35 | 5-CF₃, 2-O— pyridine | H | —CH₃ | —CH₃ | |
| 4.36 | 5-Cl, 3-F, 2-O— pyridine | H | —N(CH₃)₂ | H | |
| 4.37 | 5-CF₃, 3-Cl, 2-O— pyridine | 6-Cl | —CH₃ | —CH₃ | |
| 4.38 | 5-CF₃, 2-O— pyridine | H | —N(CH₃)₂ | H | |
| 4.39 | 5-Cl, 3-F, 2-O— pyridine | 6-CF₃ | —N(CH₃)₂ | benzyl | |
| 4.40 | 5-CF₃, 2-O— pyridine | H | —N(CH₃)₂ | —C₃H₇-n | |
| 4.41 | 5-Cl, 3-F, 2-O— pyridine | H | —N(CH₃)₂ | —CH₃ | |
| 4.42 | 5-Cl, 3-F, 2-O— pyridine | 6-CF₃ | —N(CH₃)₂ | H | |
| 4.43 | 5-CF₃, 2-O— pyridine | 6-F | —N(CH₃)₂ | H | |
| 4.44 | 5-CF₃, 3-Cl, 2-O— pyridine | 6-Cl | —N(CH₃)₂ | H | |

TABLE 4-continued

Compounds of the formula

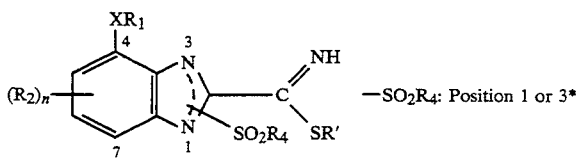
—SO$_2$R$_4$: Position 1 or 3*

| Comp. No. | R$_1$X | (R$_2$)$_n$ | R$_4$ | R' | Physical data |
|---|---|---|---|---|---|
| 4.45 | 5-Cl, 3-CF$_3$, 2-pyridyl-O— | 6-CF$_3$ | —N(CH$_3$)$_2$ | —CH$_3$ | |
| 4.46 | 5-CF$_3$, 2-pyridyl-O— | 6-F | —N(CH$_3$)$_2$ | —CH$_3$ | |
| 4.47 | 5-Cl, 3-F, 2-pyridyl-O— | 6-F | —N(CH$_3$)$_2$ | H | |
| 4.48 | 5-CF$_3$, 2-pyridyl-O— | 6-F | —N(CH$_3$)$_2$ | 4-chlorobenzyl | |
| 4.49 | 5-CF$_3$, 3-Cl, 2-pyridyl-O— | 6-Cl | —N(CH$_3$)$_2$ | —C$_2$H$_5$ | |
| 4.50 | 5-Cl, 3-F, 2-pyridyl-O— | 6-F | —N(CH$_3$)$_2$ | —CH$_3$ | |
| 4.51 | 5-CF$_3$, 3-Cl, 2-pyridyl-O— | 6-CF$_3$ | —N(CH$_3$)$_2$ | H | |
| 4.52 | 5-CF$_3$, 3-Cl, 2-pyridyl-O— | 6-CH$_3$ | —N(CH$_3$)$_2$ | —CH$_3$ | |
| 4.53 | 5-Cl, 3-F, 2-pyridyl-O— | 6-F | —N(CH$_3$)$_2$ | —C$_3$H$_7$-i | |
| 4.54 | 3-Cl, 2-pyridyl-S— | H | —N(CH$_3$)$_2$ | CH$_3$ | |
| 4.55 | 5-CF$_3$, 2-pyridyl-S— | 6-Br | —N(CH$_3$)$_2$ | H | |

TABLE 4-continued

Compounds of the formula

[Structure: benzimidazole core with XR₁ at position 4, (R₂)ₙ on benzene ring (positions 5-7), C(=NH)SR' group at position 2, and —SO₂R₄ at position 1 or 3*]

| Comp. No. | R₁X | (R₂)ₙ | R₄ | R' | Physical data |
|---|---|---|---|---|---|
| 4.56 | 6-methoxy-2-pyridyl-S— (CH₃O on pyridine, S— linker) | 5-Cl | —CH₃ | H | |
| 4.57 | 5-CF₃-3-Cl-2-pyridyl-S— | H | —CH₃ | H | |
| 4.58 | 5-CF₃-3-Cl-2-pyridyl-S— | 6-CF₃ | —N(CH₃)₂ | —CH₃ | |
| 4.59 | 3,5-diCl-2-pyridyl-S— | 5-Br | —N(CH₃)₂ | —CH₃ | |
| 4.60 | 4,6-dimethyl-2-pyrimidinyl-S— | H | —CH₃ | —CH₃ | |
| 4.61 | 4,6-dimethoxy-2-pyrimidinyl-S— | 5-OMe | —N(CH₃)₂ | H | |
| 4.62 | 4,6-dimethoxy-2-methoxy-5-pyrimidinyl-S— (CH₃O, CH₃O on pyrimidine, S— at 5-position) | H | —N(CH₃)₂ | H | |
| 4.63 | 2-pyrazinyl-S— | 5-OCF₃ | —CH₃ | —CH₃ | |
| 4.64 | 3,6-dimethyl-2-pyrazinyl-S— | H | —CH₃ | —CH₃ | |

*Isomer mixtures AB with regard to —SO₂R₄ in position 1 or 3, or the pure isomers A or B.

Formulation examples of active ingredients of the formula I (%=per cent by weight)

| 2.1. Wettable powders | a) | b) | c) |
|---|---|---|---|
| Active ingredient from the tables | 25% | 50% | 75% |

2.1. Wettable powders

|  | a) | b) | c) |
|---|---|---|---|
| Sodium ligninsulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 mol of ethylene oxide) | — | 2% | — |
| Highly-disperse silica | 5% | 10% | 10% |
| Kaolin | 62% | 27% | — |

The active ingredient is mixed thoroughly with the additives and ground thoroughly in a suitable mill. This gives wettable powders which can be diluted with water to give suspensions of any desired concentration.

2.2. Emulsion concentrate

| | |
|---|---|
| Active ingredient from the tables | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 34% |
| Xylene mixture | 50% |

Emulsions of any desired dilution can be prepared from this concentrate by dilution with water.

2.3. Dusts

|  | a) | b) |
|---|---|---|
| Active ingredient from the tables | 5% | 8% |
| Talc | 95% | — |
| Kaolin | — | 92% |

Ready-for-use dusts are obtained by mixing the active ingredient with the carrier and grinding the mixture in a suitable mill.

2.4. Extruder granules

| | |
|---|---|
| Active ingredient from the tables | 10% |
| Sodium ligninsulfonate | 2% |
| Carboxymethyl cellulose | 1% |
| Kaolin | 87% |

The active ingredient is mixed with the additives, and the mixture is ground and moistened with water. This mixture is extruded and subsequently dried in a stream of air.

2.5. Coated granules

| | |
|---|---|
| Active ingredient from the tables | 3% |
| Polyethylene glycol (MW 200) | 3% |
| Kaolin | 94% |

(MW = molecular weight)

In a mixer, the finely ground active ingredient is applied uniformly to the kaolin which has been moistened with polyethylene glycol. In this manner, dust-free coated granules are obtained.

2.6. Suspension concentrate

| | |
|---|---|
| Active ingredient from the tables | 40% |
| Ethylene glycol | 10% |
| Nonylphenol polyethylene glycol ether (15 mol of ethylene oxide) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. In this manner, a suspension concentrate is obtained from which suspensions of any desired concentration can be prepared by dilution with water.

3. Biological examples

Example 3.1: Action against *Plasmopara viticola* on grape vines a) Residual-protective action Grapevine seedlings in the 4–5-leaf stage are sprayed with a spray mixture prepared with a wettable powder of the active ingredient (0.02% of active ingredient). After 24 hours, the treated plants are infected with a sporangia suspension of the fungus. The fungus infestation is assessed after incubation for 6 days at 95–100% relative atmospheric humidity and 20° C.

b) Residual-curative action

Grapevine seedlings in the 4–5-leaf stage are infected with a sporangia suspension of the fungus. After incubation for 24 hours in a humid chamber at 95–100% relative atmospheric humidity and 20° C., the infected plants are dried and sprayed with a spray mixture prepared with a wettable powder of the active ingredient (0.02% of active ingredient). After the spray coating has dried on, the treated plants are returned to the humid chamber. The fungus infestation is assessed 6 days after the infection.

Compounds from the tables exhibit very good activity against *Plasmopara viticola* on grapevines, in particular active ingredients Nos. 1.2, 1.24, 1.66, 1.250, 1.276, 1.303, 1.322, 1.346, 3.79 and others cause complete suppression of fungus infestation (residual infestation 0 to 5%). In contrast, the Plasmopara infestation of untreated, but infected, control plants was 100%.

Example 3.2: Action against Phytophthora on tomato plants

Residual-protective action

Tomato plants which have been grown for 3 weeks are sprayed with a spray mixture prepared with a wettable powder of the active ingredient (0.02% of active ingredient). After 24 hours, the treated plants are infected with a sporangia suspension of the fungus. The fungus infestation is assessed after incubation of the infected plants for 5 days at 90–100% relative atmospheric humidity and 20° C.

Compounds from the tables exhibit a sustained activity (fungus infestation less than 20%). Compounds Nos. 1.2, 1.12, 1.23, 1.24, 1.26, 1.54, 1.66, 1.146, 1.177, 1.199, 1.221, 1.230, 1.275, 1,308, 3.50, 3.79 and others virtually completely prevent inferration (0 to 5% infestation). In contrast, the Phytophthora infestation of untreated, but infected. control plants is 100%.

Example 3.3: Action against Phytophthora on potato plants

Residual-protective action 2-3-week-old potato plants (cultivar Bintie) are grown for 3 weeks and then sprayed with a spray mixture prepared with a wettable powder of the active ingredient (0.02% of active ingredient). After 24 hours, the treated plants are infected with a sporangia suspension of the fungus. The fungus infestation is assessed after incubation of the infected planus for 5 days at 90-100% relative atmospheric humidity and 20° C.

Compounds from the tables exhibit a sustained activity (fungus infestation below 20% ), Compounds No.s 1.23, 1.24, 1.66, 1.146 and others prevent infestation virtually completely (0 to 5% infestation). In contrast, the Phytophthora infestation of untreated, but infected, control plants is 100%.

Example 3.4: Action against *Pythium debaryanum* on sugar beet (*Beta vulgaris* )

a) Action after soil drench

The fungus is cultured on sterile oat grains and added to a mixture of soil and sand. The soil which has been infected in this manner is filled into flower pots and sugar beet seeds are sown in. Immediately after sowing, the test preparations which are formulated as wettable powders are poured over the soil in the form of an aqueous suspension (20 ppm of active ingredient based on the soil volume). Hereupon, the pots are placed in the greenhouse for 2-3 weeks at 20°-24° C. The soil is constantly kept uniformly moist by gently spraying it with water. In the evaluation of the test, the emergence of the sugar beet plants as well as the quantity of healthy and diseased plants are determined.

b) Action after application by seed-dressing

The fungus is cultured on sterile oat grains and added to a mixture of soil and sand. The soil which has been infected in this manner is filled into flower pots and sugar beet seeds are sown in, which had been treated with the test preparations formulated as powders for seed-dressing (1000 ppm of active ingredient based on the seed weight). Hereupon, the pots in which the seeds have been sown are placed in the greenhouse at 20°-24° C. for 2-3 weeks. The soil is constantly kept uniformly moist by gently spraying it with water. In the evaluation of the test, the emergence of the sugar beet plants as well as the quantity of healthy and diseased plants are determined.

After treatment with the active ingredients of the formula I of Tables 1 and 3, more than 80% of the plants emerge and are healthy in appearance. Only a few plants emerge in the control pots, and their appearance is unhealthy.

Example 3.5: Direct action against *Peronospora tabacina*

Formulated active ingredient in a range of concentrations (10, 1, 0.1 ppm) is mixed with agar prepared with water, and the agar mixture is poured into Petri dishes. After cooling, 100 μl of a sporangia suspension ($10^6$ spores/ml) are streaked onto the plate. The plates are incubated for 16 hours at 18° C.

Compounds of Tables 1 and 3 were not found to inhibit the germination of *Peronospora tabacina*.

What is claimed is:

1. A compound of formula I

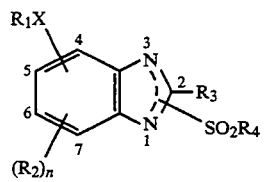

in which the $R_4SO_2$ group occupies the 1-position or the 3-position, or a mixture of the two positional isomers of formula I, relative to the substituents $R_1X$- $R_2$, wherein $R_1$ is an unsaturated 5-membered heterocycle having not more than two hetero atoms selected from the group consisting of nitrogen and sulfur, or an unsaturated 6-membered heterocycle having not more than two N atoms, wherein each of the heterocyclic radicals is unsubstituted or substituted by at least one of the substitutents selected from the group consisting of halogen, $C_1$-$C_3$alkyl, $C_1$-$C_3$alkoxy, $C_1$-$C_3$haloalkyl, $C_1$-$C_3$haloalkoxy, $COOC_1$-$C_3$alkyl, $C_3$-$C_6$cycloalkyl, cyano and nitro;

$R_2$ radicals, identical or different, are halogen, $C_1$-$C_3$alkyl, $C_1$-$C_3$alkoxy, $C_1$-$C_3$haloalkyl, $C_1$-$C_3$haloalkoxy, nitro;

$R_3$ is cyano, —CS—$NH_2$ or —C(SR')=NH, where R' is $C_1$-$C_4$alkyl, $C_1$-$C_4$haloalkyl, or benzyl which is unsubstituted or substituted by halogen, trifluoromethyl or both;

$R_4$ is $C_1$-$C_4$alkyl, $C_3$-$C_6$cycloalkyl, —N(R'')(R'''), in which R'' and R''' are indentical or different $C_1$-$C_3$alkyl radicals;

X is oxygen or sulfur; and n is an integer 0, 1 or 2.

2. A compound of claim 1 wherein $R_1$ is an unsaturated 5-membered heterocyclic radical having no more than two hetero atoms selected from the group consisting of nitrogen and sulfur, or an unsaturated 6-membered heterocyclic radical having no more than two N atoms, wherein each of the heterocyclic radicals is unsubtituted or substituted by at least one substituent selected from the group consisting of halogen, $C_1$-$C_3$alkyl, $C_1$-$C_3$alkoxy $C_1$-$C_3$haloalkyl, $C_1$-$C_3$haloalkoxy and nitro.

3. A compound of claim 2 wherein R' is an unsubstituted or substituted pyridyl, pyrimidyl, pyrazyl or pyridazyl.

4. A compound of claim 3, wherein $R_1$ is the 6-membered heterocyclic radical, unsubstituted or substituted by one to three substituents selected from the group consisting of halogen, methyl, ethyl, isopropyl, methoxy, $C_1$-$C_2$fluoroalkyl, $C_1$-$C_2$chloroalkyl, trifluoromethoxy, difluoromethoxy and nitro.

5. A compound of claim 4, wherein the 6-membered heterocyclic radical is unsubstituted or mono- to trisubstituted pyridyl and the $R_2$ radicals, are identical or different, and are fluorine, chlorine, bromine, methyl, methoxy, trifluoromethyl, trifluoromethoxy or difluoromethoxy.

6. A compound of claim 5, in which $R_2$ is fluorine, chlorine, bromine or trifluoromethyl.

7. A compound of claim 6, in which the pyridyl ring is substituted by $CF_3$.

8. A compound of claim 3, wherein $R_1$ is pyrimidyl which is unsubstituted or substituted by halogen, $C_1$-$C_4$alkyl, $C_1$-$C_4$alkoxy or $C_1$-$C_2$haloalkyl, and $R_2$ is fluorine, chlorine, bromine, methyl, methoxy, trifluoromethyl or trifluoromethoxy.

9. A compound of claim 8, wherein the pyrimidyl ring is unsubstituted or substituted by halogen or $C_1$–$C_2$-haloalkyl and $R_2$ is fluorine, chlorine, bromine, methyl, methoxy or trifluoromethyl.

10. A compound of claim 9, wherein $R_1$ is 4-pyrimidyl.

11. A compound of to claim 4, in which $R_4$ is methyl, dimethylamino, cyclopropyl, cyclopentyl or cyclohexyl.

12. A compound of claim 11, in which $R_4$ is methyl.

13. A compound of claim 11, in which $R_4$ is dimethylamino.

14. A compound of claim 2, in which $R_3$ is cyano or $C(S)NH_2$.

15. A compound of claim 2, in which $XR_1$ is in the 5 or 6-position.

16. A compound of claim 2, in which R1 is an unsubstituted or substituted 5-membered heterocyclic radical selected from the group consisting of pyrrolyl, thienyl, thiazolyl, isothiazolyl, imidazolyl and pyrazolyl.

17. A compound of claim 16, in which the 5-membered heterocyclic radical is substituted by halogen and/or methyl.

18. A compound of claim 16, in which $R_2$ radicals, identical or different, are halogen, methyl, methoxy, $CF_3$, $CF_3O$ or $CHF_2O$.

19. A compound of claim 2, in which X is oxygen.

20. A compound of claim 2, in which X is sulfur.

21. A composition for controlling and preventing attack of plants by phytopathogenic fungi, which comprises, as active ingredient, an effective amount of a compound of claim 2 together with a carrier.

22. A composition for controlling and preventing an attack of plants by phytopathogenic fungi which comprises an inert carrier and, as active ingredient, an effective amount of a compound of claim 3.

23. A composition for controlling and preventing an attack of plants by phytopathogenic fungi which comprises an inert carrier and, as active ingredient, an effective amount of a compound of claim 4.

24. A method of controlling and preventing attack of plants by phytopathogenic fungi, which comprises applying an effective amount of a compound of formula I:

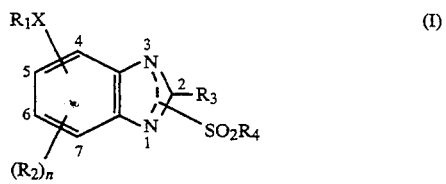

in which the $R_4SO_2$ group occupies the 1-position or the 3-position, or a mixture of the two positional isomers of formula I, relative to the substituents $R_1X$- and $R_2$, $R_1$ is an unsaturated 5-membered heterocycle having not more than two hetero atoms selected from the group consisting of nitrogen and sulfur, or an unsaturated 6-membered heterocycle having not more than two N atoms, wherein each of the heterocyclic radicals is unsubstituted or substituted by at least one of the substituents selected from the group consisting of halogen, $C_1$–$C_3$alkyl, $C_1$–$C_3$alkoxy, $C_1$–$C_3$haloalkyl, $C_1$–$C_3$haloalkoxy, $COOC_1$–$C_3$alkyl, $C_3$–$C_6$cycloalkyl, cyano and nitro;

$R_2$ radicals, identical or different, are halogen, $C_1$–$C_3$alkyl, $C_1$–$C_3$alkoxy, $C_1$–$C_3$haloalkyl, $C_1$–$C_3$haloalkoxy, nitro;

$R_3$ is cyano, —CS—$NH_2$ or —C(SR')=NH, where R' is $C_1$–$C_4$alkyl, $C_1$–$C_4$haloalkyl, or benzyl which is unsubstituted or substituted by halogen, trifluoromethyl or both;

$R_4$ is $C_1$–$C_4$alkyl, $C_3$–$C_6$cycloalkyl, —N(R")(R'''), in which R" and R''' are identical or different $C_1$–$C_3$alkyl radicals;

X or oxygen or sulfur; and n is an integer 0, 1 or 2; to the plant, parts of the plant or the substrate of the plant.

* * * * *